United States Patent
Piccotti et al.

(10) Patent No.: US 11,260,020 B2
(45) Date of Patent: *Mar. 1, 2022

(54) TOPICAL COMPOSITIONS AND METHODS FOR REDUCING OXIDATIVE STRESS

(71) Applicant: Kimberly-Clark Worldwide, Inc., Neenah, WI (US)

(72) Inventors: Lucia Piccotti, Houston, TX (US); David J. Tyrrell, Milwaukee, WI (US); Penkanok Sriwiriyanont, Neenah, WI (US); Debbie Ngai, Neenah, WI (US); Josh Gregorio, Neenah, WI (US); Scott W. Wenzel, Neenah, WI (US); Rebecca Uelmen, Greenville, WI (US); Seungjun 'Jason' Lee, Neenah, WI (US)

(73) Assignee: Kimberly-Clark Worldwide, Inc., Neena, WI (US)

( * ) Notice: Subject to any disclaimer, the term of this patent is extended or adjusted under 35 U.S.C. 154(b) by 412 days.

This patent is subject to a terminal disclaimer.

(21) Appl. No.: 15/304,818

(22) PCT Filed: Apr. 30, 2014

(86) PCT No.: PCT/US2014/036199
§ 371 (c)(1),
(2) Date: Oct. 17, 2016

(87) PCT Pub. No.: WO2015/167542
PCT Pub. Date: Nov. 5, 2015

(65) Prior Publication Data
US 2017/0042799 A1 Feb. 16, 2017
US 2018/0064633 A9 Mar. 8, 2018
US 2018/0344622 A9 Dec. 6, 2018

(51) Int. Cl.
*A61K 8/9711* (2017.01)
*A61Q 19/08* (2006.01)
*A61K 36/03* (2006.01)
*A61K 36/28* (2006.01)
*A61Q 19/00* (2006.01)
*A61K 9/00* (2006.01)
*A61K 8/9789* (2017.01)

(52) U.S. Cl.
CPC .......... *A61K 8/9711* (2017.08); *A61K 8/9789* (2017.08); *A61K 9/0014* (2013.01); *A61K 36/03* (2013.01); *A61K 36/28* (2013.01); *A61Q 19/004* (2013.01); *A61Q 19/08* (2013.01); *A61K 2800/10* (2013.01); *A61K 2800/522* (2013.01)

(58) Field of Classification Search
CPC ................................ A61K 36/03; A61K 36/20
USPC .......................................... 424/195.18, 778
See application file for complete search history.

(56) References Cited

U.S. PATENT DOCUMENTS

| | | |
|---|---|---|
| 3,296,145 A | 1/1967 | Findlan et al. |
| 5,387,208 A | 2/1995 | Ashton et al. |
| 5,804,206 A | 9/1998 | D'Amelio et al. |
| 5,925,615 A | 7/1999 | Kern et al. |
| 5,939,078 A * | 8/1999 | Fujimura ................. A61K 8/43 424/401 |
| 5,955,407 A | 9/1999 | Davister et al. |
| 6,613,030 B1 | 9/2003 | Coles et al. |
| 6,616,922 B2 | 9/2003 | Taylor et al. |
| 7,842,232 B2 | 11/2010 | Bosch et al. |
| 8,101,211 B2 | 1/2012 | Chiba et al. |
| 8,496,948 B2 | 7/2013 | Harripersad |
| 8,568,752 B2 | 10/2013 | Schultz |
| 8,580,741 B2 | 11/2013 | Lee et al. |
| 10,548,835 B2 * | 2/2020 | Wenzel ................. A61Q 19/08 |
| 10,646,430 B2 * | 5/2020 | Wenzel ............... A61Q 19/005 |
| 2001/0044393 A1 | 11/2001 | Peterson, Jr. et al. |
| 2002/0028227 A1 | 3/2002 | Yu et al. |
| 2002/0098218 A1 | 7/2002 | Zhuang et al. |
| 2003/0021850 A1 | 1/2003 | Xu |
| 2003/0185869 A1 | 10/2003 | Wertz et al. |
| 2003/0190337 A1* | 10/2003 | Bissett ..................... A61K 8/64 424/401 |
| 2004/0028643 A1* | 2/2004 | Chiba ..................... A61K 8/97 424/74 |
| 2005/0048008 A1 | 3/2005 | Gupta |
| 2007/0179207 A1 | 8/2007 | Fernandez de Castro et al. |
| 2007/0248563 A1 | 10/2007 | Iovanni et al. |
| 2007/0292461 A1 | 12/2007 | Tamarkin et al. |
| 2008/0112968 A1 | 5/2008 | Gebicki |
| 2008/0241070 A1 | 10/2008 | Ryde et al. |
| 2009/0012049 A1 | 1/2009 | Fabre et al. |

(Continued)

FOREIGN PATENT DOCUMENTS

BR 201003665 A2 * 3/2012
BR PI1003665 A2 3/2012

(Continued)

OTHER PUBLICATIONS

Hyun et al., "Photoprotective effective of Undaria crenata against ultraviolet B-induced damage to kerantinocytes", Journal of Bioscience and Bioengineering, vol. 116 No. 2, 256-264, 2013 (Year: 2013) (Year: 2013).*
Pandel et al. Skin Photoaging and the Role of Antioxidants in Its Prevention, (ISRN Dermatology, vol. 2013, Article ID 930164, 11 pages). (Year: 2013).*
Cardenas et al. "Toxicological Evaluation of An Infusion of Bidens pilosa" Pharmacologyonline 3: 428-434 (2006) (Year: 2010).*
Hyun et al, "Photoprotective effect of Undaria crenata against ultraviolet B-induced damage to kerantinocytes", Journal of Bioscience and Bioengineering, vol. 116 No. 2, 256-264, 2013 (Year: 2013).*

(Continued)

*Primary Examiner* — Michael Barker
(74) *Attorney, Agent, or Firm* — Armstrong Teasdale LLP

(57) ABSTRACT

Compositions for reducing skin aging resulting from oxidative stress and/or photodamage are disclosed herein. The compositions can be topically applied to a skin region to reduce or prevent skin wrinkles, fine lines, thinning skin, sagging skin, skin dryness, and skin itchiness.

26 Claims, 18 Drawing Sheets

(56) References Cited

U.S. PATENT DOCUMENTS

| | | |
|---|---|---|
| 2009/0318322 A1 | 12/2009 | Taylor et al. |
| 2010/0099640 A1 | 4/2010 | Geuns et al. |
| 2011/0086088 A1 | 4/2011 | Berry |
| 2011/0129453 A1 | 6/2011 | Harripersad |
| 2011/0144214 A1 | 6/2011 | Snyder et al. |
| 2011/0262505 A1* | 10/2011 | Athwal ............... A61K 8/73 424/401 |
| 2012/0070341 A1 | 3/2012 | Eder et al. |
| 2012/0107427 A1 | 5/2012 | Kim et al. |
| 2013/0017239 A1 | 1/2013 | Viladot Petit et al. |
| 2013/0059929 A1 | 3/2013 | Koehler et al. |

FOREIGN PATENT DOCUMENTS

| | | |
|---|---|---|
| CN | 101621984 A | 1/2010 |
| DE | 202012005442 U1 | 7/2012 |
| EP | 0965323 A2 | 12/1999 |
| EP | 1649873 A2 | 4/2006 |
| JP | 11269036 A | 10/1999 |
| JP | 2001335422 A | 12/2001 |
| JP | 2004083442 A | 3/2004 |
| JP | 4073358 B2 | 11/2004 |
| JP | 2004323362 A | 11/2004 |
| JP | 2009057290 A | 3/2009 |
| KR | 20090005839 A | 1/2009 |
| KR | 2013106712 A | 9/2013 |
| KR | 1020140036400 A | 4/2014 |
| WO | 0126595 A1 | 4/2001 |
| WO | 02087645 A1 | 11/2002 |
| WO | 03018732 A1 | 3/2003 |
| WO | 2005047445 A1 | 5/2005 |
| WO | 2008096203 A2 | 8/2008 |
| WO | 2009098476 A1 | 8/2009 |
| WO | 2009109869 A2 | 9/2009 |
| WO | 2010039291 A1 | 4/2010 |
| WO | 2010127231 A2 | 11/2010 |
| WO | 2011124241 A2 | 10/2011 |
| WO | 2012145609 A1 | 10/2012 |
| WO | 2015167542 A2 | 11/2015 |

OTHER PUBLICATIONS

B.W. Barry, "Action of Skin Penetration Enhancers—the Lipid Protein Partioning Theory", International Journal of Cosmetic Science 10, 281-293 (Year: 1988).*

Chemyunion: Richesses D'Amazonie, Parfums Cosmetiques Actualites, "The Wealth of the Amazon", Sep. 2009, KOSMET database Abstract, 1 page.

Hu et al., "Antioxidant activity of sulfated polysaccharide fractions extracted from Undaria pinnitafida in vitro", International Journal of Biological Macromolecules, Mar. 1, 2010, vol. 46, No. 2, pp. 193-198.

Hyun, Y. J., "Photoprotective effect of Undaria crenata against ultraviolet B-induced damage to keratinocytes", Journal of Bioscience and Bioengineering, Mar. 6, 2013, vol. 116, No. 2, pp. 256-264.

Kim et al., "Fucoidan from the sporophyll of Undaria pinnatifida suppresses adipocyte differentiation by inhibition of inflammation-related cytokines in 3T3-L1 cells", Nutrition Research, May 18, 2012, vol. 32, No. 6, pp. 439-447.

Yang et al., "Protection from oxidative damage using Bidens pilosa extracts in normal human erythrocytes", Food and Chemical Toxicology, Sep. 2006, vol. 44, No. 9, pp. 1513-1521.

International Search Report and Written Opinion for International Application No. PCT/US2014/036199, dated Feb. 29, 2016, 10 pages.

International Preliminary Report on Patentability for International Patent Application No. PCT/US14/36199, dated Jul. 15, 2016, 7 pages.

International Search Report and Written Opinion for International Application No. PCT/US2014/036206, dated Jan. 29, 2015, 12 pages.

International Preliminary Report on Patentability for International Patent Application No. PCT/US2014/036206, dated Apr. 25, 2016, 5 pages.

International Search Report and Written Opinion for International Application No. PCT/US2014/036210, dated Jan. 15, 2015, 12 pages.

International Preliminary Report on Patentability for International Patent Application No. PCT/US2014/036210, dated Jul. 11, 2016, 6 pages.

International Search Report and Written Opinion for International Application No. PCT/US2014/036216, dated Jan. 15, 2015, 14 pages.

International Preliminary Report on Patentability for International Patent Application No. PCT/US2014/036216, dated Apr. 7, 2016, 7 pages.

International Search Report and Written Opinion for International Application No. PCT/US2014/036223, dated Jan. 29, 2015, 9 pages.

International Preliminary Report on Patentability for International Patent Application No. PCT/US2014/036223, dated Apr. 28, 2016, 5 pages.

International Search Report and Written Opinion for International Application No. PCT/US2014/036233, dated Jan. 28, 2015, 14 pages.

International Preliminary Report on Patentability for International Patent Application No. PCT/US2014/036233, dated Apr. 29, 2016, 6 pages.

International Search Report and Written Opinion for International Application No. PCT/US2014/036242, dated Jan. 15, 2015, 13 pages.

International Preliminary Report on Patentability for International Patent Application No. PCT/US2014/036242, dated Apr. 12, 2016, 5 pages.

Derwent Abstract of BR 201003665 A2, retrieved on Jan. 15, 2019, 2 pages.

Koster et al., "Rwandan female genital modification: Elongation of the Labia Minora and the use of local botanical species", Culture, Health & Sexuality, vol. 10, No. 2, pp. 191-204.

Office Action issued in GB 1618949.0, dated Feb. 6, 2018, 6 pages.

Science in Nature, Chemyunion Quimica LTDA, http://www.incosmetics.com/_novadocuments/9242, 6 pages.

AspireLIFE, Active Ingredients Efficacy Report, published Aug. 2012, Available on: https://cdn.shopify.com/s/files/1/0150/6346/files/AspireLIFE_Efficacy_Report_aug_2012_red_size, 29 pages.

Cardenas et al., "Toxicological evaluation of an infusion of Bidens pilosa". Pharmacologyonline, 2006, vol. 3, pp. 428-434.

Descriptive Note: "New natural ingredients directory. Ecobidens." Available in: https://www.happi.com/contents/view_features/2010-07-08/new-natural-ingredients-directory, Published: Jul. 8, 2010, 25 pages.

Ziouzenkova et al., "Retinoid metabolism and nuclear receptor responses: New Insights into coordinated regulation of the PPAR-RXR complex", FEBS Letters, 2008, vol. 582, pp. 32-38.

Brand et al., "A Single Oral Dose of Ethanol Can Alter Transdermal Absorption of Topically Applied Chemicals in Rats", Toxicological Sciences, 2006, vol. 92, No. 2, pp. 349-355.

Fluhr et al., "Glycerol and the skin: holistic approach to its origin and functions", British Journal of Dermatology, 2008, vol. 159, pp. 23-34.

Gupta et al., "Anti-Inflammatory and Antipyretic Activities of β-Sitolsterol, J Medicinal Plant Research", 1980, vol. 39, pp. 157-163.

* cited by examiner

TOPICAL COMPOSITIONS AND METHODS FOR REDUCING OXIDATIVE STRESS

BACKGROUND OF THE DISCLOSURE

The present disclosure relates generally to compositions and methods for enhancing cellular response to oxidative stress and photodamage, and in particular, enhancing cellular response in dermal fibroblasts and epidermal keratinocytes, which can result in signs of skin aging of the face and body. More particularly, the present disclosure relates to compositions including an *Undaria* extract and/or *Bidens* extract and methods of topically applying the compositions for enhancing cellular mitochondrial activity and antioxidant cellular response to oxidative stress and UV irradiation, thereby reducing signs of aging of the face and body. Signs of aging that affect the skin of the face and body include, for example, wrinkles, fine lines, thinning skin, sagging skin, skin dryness and skin itchiness.

With respect to skin aging, a distinction is made between so-called "intrinsic" and "extrinsic" aging, a decisive factor for the latter being the exogenous effect, in particular the effect of ultraviolet (UV) radiation ("photoaging"). Mechanistically, oxidative stress plays a major role in both intrinsic and extrinsic aging of the skin since reactive oxygen species (ROS) are generated in the process of normal cellular metabolism or by physiological processes and, particularly, are produced by the UVA and UVB components of UV radiation. If not suppressed upon formation, ROS have far-reaching effects on the integrity of all cellular biomolecules such as DNA, proteins and lipids with regard to UV-induced aging of the skin. Particularly, overproduction of ROS can lead to lipid peroxidation, damage to biomolecules, and effects on cellular viability. An immediate consequence of particular importance in photoaging is the ROS induction of matrix metalloproteinases that increases degradation of collagen proteins, creating an imbalance between collagen synthesis and degradation, leading to skin thinning Thus far, strategies for preventing photoaging consist of a reduction in UV-exposure, physical protection from UV-exposure and/or the application of specific vitamins, such as vitamin C or vitamin E.

Particularly, a wide variety of creams and lotions exist that can cosmetically improve the appearance, and sometimes, the structure of the skin on the face and body. Such compositions often employ retinoids, hydroxy acids and/or exfoliants to encourage skin rejuvenation, increase firmness or otherwise cosmetically improve the skin. Many cosmetic products provide moisture and can enhance the skin's appearance by plumping the skin using irritants that cause inflammation. Other cosmetic products are available that claim to rejuvenate and create a more youthful appearance by targeting extracellular matrix proteins such as elastin and collagen, which are produced by fibroblasts to provide skin strength and resilience.

Medical procedures, such as dermal injections and reconstructive surgery, are also available to reduce the signs of aging. Cosmetic surgery has recently grown in popularity to aesthetically enhance the appearance of skin. These procedures, however, are not always desirable options as surgery can be costly, painful and very invasive.

While the cosmetic products and medical procedures described above are suitable for treating aged skin of the face and body, alternative compositions and methods for improving skin are desirable. Accordingly, there exists a need to develop alternative compositions and methods for preventing and/or reducing oxidative stress that can lead to increased signs of skin aging of the face and body. It would be highly advantageous if the compositions and methods could be topically applied such that invasive, painful, and costly medical procedures could be avoided.

BRIEF DESCRIPTION OF THE DISCLOSURE

The present disclosure is generally directed to compositions and methods for enhancing the cellular response to photoaging and oxidative stress such to reduce the effects of UV irradiation, oxidative stress and oxidative stress-induced apoptosis of skin cells, and in particular, dermal fibroblasts and epidermal keratinocytes. These negative effects on cells can result in increased signs of skin aging on the face and body.

In one aspect, the present disclosure is directed to a method for reducing oxidative stress of cells in an individual in need thereof. The method includes topically applying a composition that comprises at least one active agent selected from the group consisting of an *Undaria* extract and a *Bidens* extract, and a hydrophilic carrier to a target skin region of the individual.

In another aspect, the present disclosure is directed to a method for reducing oxidative stress-induced apoptosis of cells in an individual in need thereof. The method includes topically applying a composition that comprises at least one active agent selected from the group consisting of an *Undaria* extract and a *Bidens* extract, and a hydrophilic carrier to a target skin region of the individual.

In yet another aspect, the present disclosure is directed to a method for reducing photodamage of cells in an individual in need thereof. The method includes topically applying a composition that comprises at least one active agent selected from the group consisting of an *Undaria* extract and a *Bidens* extract, and a hydrophilic carrier to a target skin region of the individual.

In yet another aspect, the present disclosure is directed to a method for maintaining cellular glutathione concentration of cells in an individual in need thereof. The method includes topically applying a composition that comprises at least one active agent selected from the group consisting of an *Undaria* extract and a *Bidens* extract, and a hydrophilic carrier to a target skin region of the individual.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 3A represents control fibroblasts; FIG. 3B represents fibroblasts treated with $H_2O_2$ for 1 hour; FIG. 3C represents fibroblasts treated with UNDARINE™ for 12 hours; and FIG. 3D represents fibroblasts treated with UNDARINE™ for 12 hours followed by exposure to $H_2O_2$ for 1 hour.

FIG. 6A represents control fibroblasts; FIG. 6B represents fibroblasts treated with $H_2O_2$ for 1 hour; FIG. 6C represents fibroblasts treated with ECOBIDENS™ for 12 hours followed by exposure to $H_2O_2$ for 1 hour; FIG. 6D represents fibroblasts treated with ECOBIDENS™ for 12 hours; FIG. 6E represents fibroblasts exposed to UV irradiation; and FIG. 6F represents fibroblasts treated with ECOBIDENS™ for 12 hours followed by exposure to UV irradiation.

Figure 1:
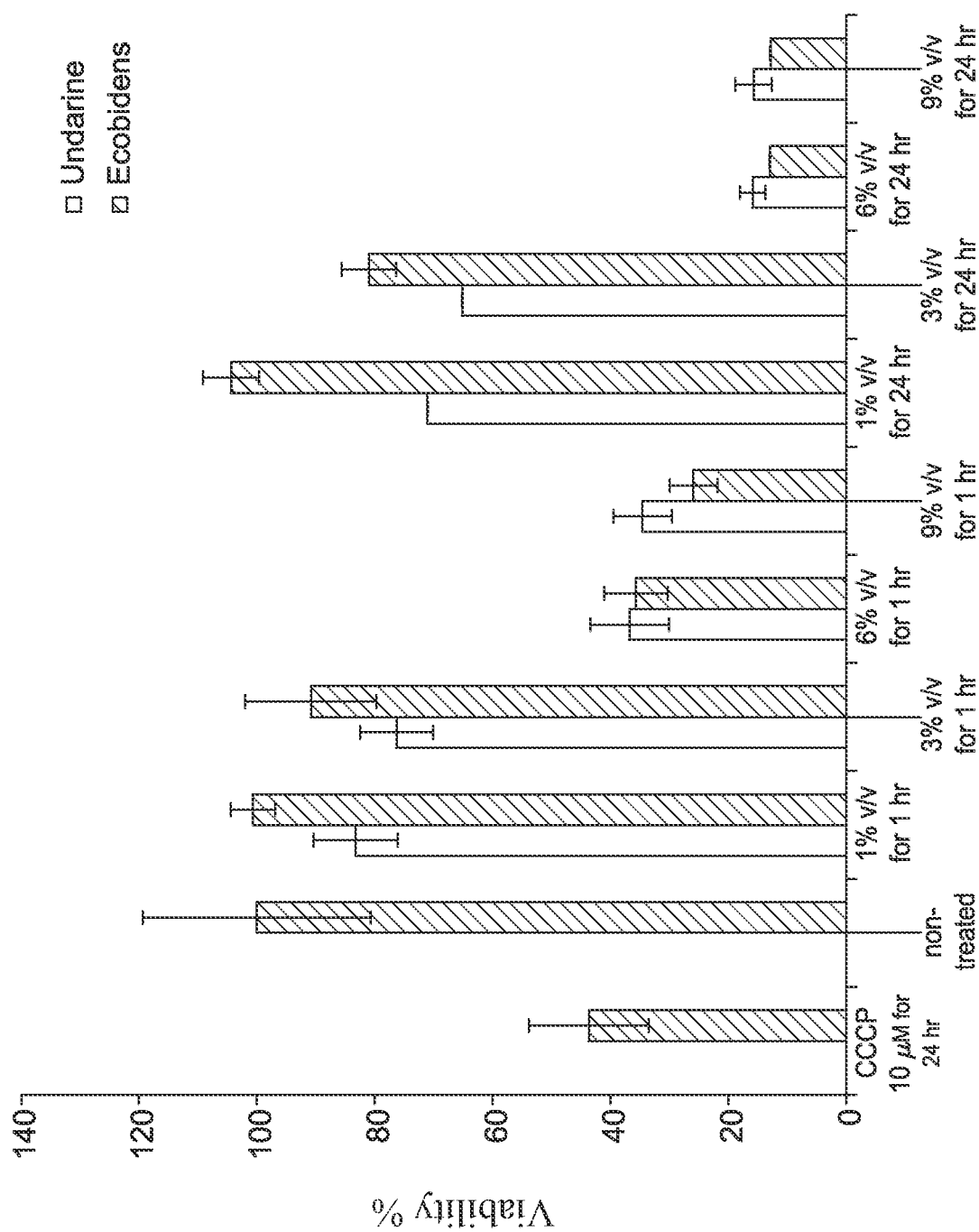
FIG. 1 is a graphical illustration showing viability following treatment of cells with various concentrations of active components as discussed in Example 1.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, compositions and methods have been discovered that surprisingly allow for reducing the signs of skin aging. The methods of the present disclosure have a broad and significant impact, as they protect cells from UV exposure and excessive production of ROS by stimulating the cellular antioxidant response (e.g., increase in reduced gluthatione concentration), thereby resulting in a more youthful appearance of aged skin of the face and body. More particularly, in the dermis, fibroblasts produce collagen and elastin, which provide skin strength and resilience. Photodamage and ROS-induced oxidative stress are among the main causes of fibroblast degeneration and death; thereby, accelerating the process of skin aging and exacerbating skin aging symptoms such as skin thinning, sagging, fragility, and loss of skin resiliency.

As used herein, "body" refers to an individual's entire body, and particularly, includes the regions of the face (including forehead, cheeks, chin, and eyelids), neck, shoulders, breast, chest, legs, hands, feet and vulvar area including vulvar skin, for example, the vulva, labia, labia majora, labia minor, mons pubis, vulval vestibule, and combinations thereof.

As used herein, "apoptosis" refers to the process of programmed cell death that may occur in multicellular organisms. Particularly, a cell initiates intracellular apoptotic signaling in response to a stress (e.g., UV irradiation, oxidative stress resulting from ROS overproduction, etc.).

COMPOSITIONS

Active Ingredients/Extracts

The present disclosure has unexpectedly found that particular extracts can be topically applied, alone or in combination, to an individual's skin as active ingredients in compositions to reduce the signs of skin aging. Particularly, while the active ingredients of the compositions have been previously known to stimulate collagen and elastin, it has now been unexpectedly found that these active ingredients are effective at protecting the skin from factors that cause extrinsic skin aging, and in particular, to protect the dermal layer from exposure to UV irradiation and ROS-induced damage. It is believed that this protective effect is due to the active agents enhancing cellular defense mechanisms, and in particular, cellular mitochondrial activity and antioxidant cellular response. This provides the user with plumper, fuller, more resilient skin and a more youthful, smoother skin appearance.

*Undaria* Extract

In one aspect, the present disclosure is directed to compositions for reducing the signs of skin aging of the face and body; the compositions generally include an *Undaria* extract as the active ingredient. As used herein, "extract" refers to the active solid components from the *Undaria* plant.

An *Undaria* extract is an extract obtained from *Undaria*, a genus of brown alga that includes *U crenata, U. peterseniana, U pinnatifida* and *U undarioides*. *Undaria* extracts are known to stimulate collagen and elastin, and have previously been described in vendor literature to increase 14 genes linked to collagen and elastin production. As disclosed herein, the *Undaria* extracts used in the compositions of the present disclosure have further surprisingly been found to protect cells, and in particular, dermal fibroblasts and epidermal keratinocytes, from photodamage and oxidative stress.

As used herein, *Undaria* extract, refers to a liquid extract from the *Undaria* plant. In particularly suitable embodiments, the *Undaria* extract has not been further supplemented/standardized for fucoidan content. Particularly, the *Undaria* extracts in these suitable embodiments are extracts obtained by soaking or passing the *Undaria* algae plants in/over water with no further chemical treatment. The soaking/passing over can be accomplished with any method known in the extraction arts, such as, for example, lixiviation, infusion steeping, percolation, extraction, and the like, and combinations thereof. In some embodiments, the *Undaria* plant could be mascerated to further obtain the extract. Additionally, the water used in these processes could be heated to obtain the *Undaria* extract.

One particularly suitable method for obtaining the *Undaria* extract is lixiviation of fertile bases from lyophilized *Undaria* algae plants. As used herein, "lixiviation" refers to a technique where water is slowly passed over a solid (here, *Undaria*) in a layer of varying depth to extract soluble material. The general technique is described in FR 2693917, which is incorporated herein to the extent it is consistent herewith, and is performed at room temperature. After removal of the extract, in some embodiments, the extract is further diluted with diluents including water, glycerin, propanediol, butylene glycol, propylene glycol and combinations thereof.

By contrast, *Undaria* extracts that are supplemented/standardized for fucoidan content typically are obtained by an extraction procedure utilizing an acid/water mixture having a pH of between 0 and 2, preferably between about 0 and 1, at temperatures between about 0 and 30° C., preferably between about 15 and 25° C.

Suitable *Undaria* extracts can be obtained from commercially available sources (e.g., Barnet Products Corp., Englewood Cliffs, N.J.; Changsha Organic Herb Inc., Hunan, China). A particularly suitable commercially available formulation including *Undaria* extract can be, for example, UNDARINE™, which is a formulation including glycerin, water and *U. pinnatifida* extract (commercially available from Barnet Products Corp., Englewood Cliffs, N.J.).

Another suitable commercially available *Undaria* extract can be, for example, the *U. pinnatifida* extract WAKAMINE® (INCI: water (and) *Undaria pinnatifida* extract), commercially available from SOLIANCE (France), which has previously been used to lighten skin and prevent age-spots.

Suitable amounts of an *Undaria* extract in the composition can be from about 0.01% (w/w) to about 10% (w/w), from about 0.05% (w/w) to about 7.5% (w/w), from about 0.1% (w/w) to about 5% (w/w), and from about 1% (w/w) to about 5% (w/w). As used herein "w/w" refers to the amount of the component "by weight of the composition".

*Bidens* Extract

In another aspect, the present disclosure is directed to a composition including a *Bidens* extract as the active agent. As used herein, "extract" refers to the active solid components from the *Bidens* plant. *Bidens* is a genus of plants in the Asteraceae family that includes many species members. *Bidens* is known to increase collagen and elastin production.

Suitable *Bidens* extracts include extracts of *Bidens alba*, *Bidens amplectens*, *Bidens amplissima*, *Bidens aristosa*, *Bidens asymmetrica*, *Bidens aurea*, *Bidens beckii*, *Bidens bidentoides*, *Bidens bigelovii*, *Bidens bipinnata*, *Bidens biternata*, *Bidens campylotheca*, *Bidens cernua*, *Bidens cervicata*, *Bidens chippii*, *Bidens conjuncta*, *Bidens connata*, *Bidens coronata*, *Bidens cosmoides*, *Bidens cynapiifolia*, *Bidens discoidea*, *Bidens eatonii*, *Bidens ferulifolia*, *Bidens forbesii*, *Bidens frondosa*, *Bidens gardneri*, *Bidens hawaiensis*, *Bidens henryi*, *Bidens heterodoxa*, *Bidens heterosperma*, *Bidens hillebrandiana*, *Bidens hyperborean*, *Bidens laevis*, *Bidens lemmonii*, *Bidens leptocephala*, *Bidens leptophylla*, *Bidens macrocarpa*, *Bidens mannii*, *Bidens mauiensis*, *Bidens maximowicziana*, *Bidens menziesii*, *Bidens micrantha*, *Bidens mitis*, *Bidens molokaiensis*, *Bidens x multticeps*, *Bidens parviflora*, *Bidens pilosa*, *Bidens polylepis*, *Bidens populifolia*, *Bidens radiate*, *Bidens reptans*, *Bidens sandvicensis*, *Bidens schimperi*, *Bidens simplicifolia*, *Bidens socorrensis*, *Bidens squarrosa*, *Bidens subalternans*, *Bidens tenuisecta*, *Bidens torta*, *Bidens trichosperma*, *Bidens triparfita*, *Bidens triplinervia*, *Bidens valida*, *Bidens vulgata*, *Bidens wiebkei*, and combinations thereof.

Particularly suitable *Bidens* extracts can be, for example, *Bidens pilosa* extract, *Bidens bipinnata* extract, and *Bidens tripartita* extract. Suitable *Bidens* extract can be obtained from commercially available sources (e.g., Chemyunion Quimica Ltd., Sao Paulo, Brazil; and Carrubba Inc., Milford, Conn.). Suitable *Bidens* extracts can also include *Bidens* extract blends with hydrophilic carriers such as for example, water, glycerin, propanediol, butylene glycol, propylene glycol and combinations thereof and *Bidens* extract blends with hydrophobic carriers such as for example natural oils, synthetic oils and combinations thereof. A particularly suitable *Bidens* extract can be, for example, ECOBIDENS™ (commercially available from Chemyunion Quimica Ltd., Sao Paulo, Brazil). ECOBIDENS™ is a glycerin extract of *Bidens pilosa* L. Other commercially available *Bidens* extracts include, for example, Water Agrimony Extract H. G., a *B. tripartita* extract from Provital Group (Spain); *Bidens* Extract M9983-WS, a *B. pilosa* extract, and *Bidens bipinnata* Extract N0061-WS, a *B. bipinnata* extract, both available from Carrubba Inc. (Milford, Conn.).

Suitable amounts of *Bidens* extract in the topical compositions can be from about 0.01% (w/w) to about 10% (w/w), from about 0.05% (w/w) to about 7.5% (w/w), from about 0.1% (w/w) to about 5% (w/w), and from about 1% (w/w) to about 5% (w/w).

*Undaria* Extract and *Bidens* Extract

In some particularly suitable aspects, the present disclosure is directed to a composition including combination of the active agents of an *Undaria* extract and a *Bidens* extract.

When used in a combination, suitable amounts of the *Undaria* extract in the composition can be from about 0.01% (w/w) to about 20% (w/w), from about 0.05% (w/w) to about 15% (w/w), and from about 0.1% (w/w) to about 10% (w/w). Suitable amounts of *Bidens* extract in the composition can be from about 0.01% (w/w) to about 20% (w/w), from about 0.05% (w/w) to about 15% (w/w), and from about 0.1% (w/w) to about 10% (w/w).

Additional Optional Ingredients

The compositions described herein can further include additional ingredients and optional ingredients.

Generally, the compositions include a carrier with the active ingredient(s).

In one embodiment, for example, the composition includes the active ingredient(s) and a hydrophilic carrier, a hydrophilic thickener, and/or a penetration enhancer. Suitable hydrophilic carriers can be, for example, water, alcohols, glycerin, glycerin derivatives, glycols, water-soluble emollients, and combinations thereof. Suitable examples of alcohols could include, but are not to be limited to, ethanol and isopropyl alcohol. Suitable examples of glycerin derivatives could include, but are not to be limited to, PEG-7 glyceryl cocoate. Suitable glycols could include, but are not to be limited to, propylene glycol, butylene glycol, pentylene glycol, ethoxydiglycol, dipropylene glycol, propanediol, and PEG-8. Suitable examples of water-soluble emollients could include, but are not to be limited to, PEG-6 Caprylic Capric Glycerides, Hydrolyzed Jojoba Esters, and PEG-10 Sunflower Glycerides.

In particularly suitable embodiments, the topical compositions are liquid compositions desirably containing water as the carrier. Suitable amounts of water can be from about 0.1% by weight of the composition to about 99.9% by weight of the composition. More typically, the amount of water can be from about 40% by weight of the composition to about 99.9% by weight of the composition. Preferably, the amount of water can be from about 60% by weight of the composition to about 99.9% by weight of the composition.

In another embodiment, the composition includes the active ingredient(s) and a hydrophobic carrier. Suitable hydrophobic carriers can be, for example, natural oils, synthetic oils and combinations thereof.

The topical compositions described herein can further include a skin penetrating enhancer or a mixture of skin penetration enhancers. Examples of suitable skin penetration enhancers include sulfoxides, alcohols, fatty acids, fatty acid esters, polyols, amides, surfactants, terpenes, alkanones, and organic acids, among others. Specific examples of suitable sulfoxides include dimethylsulfoxide (DMSO) and decylmethylsulfoxide, among others. Suitable alcohols include alkanols such as ethanol, propanol, butanol, pentanol, hexanol, octanol, n-octanol, nonanol, decanol, 2-butanol, 2-pentanol, and benzyl alcohol; fatty alcohols, such as caprylic alcohol, decyl alcohol, lauryl alcohol, 2-lauryl alcohol, myristyl alcohol, cetyl alcohol, stearyl alcohol, oleyl alcohol, linoleyl alcohol, and linolenyl alcohol; and isopropyl alcohol. Examples of suitable fatty acids include linear fatty acids such as valeric acid, heptanoic acid, pelagonic acid, caproic acid, capric acid, lauric acid, myristic acid, stearic acid, oleic acid, and caprylic acid; and branched fatty acids, such as isovaleric acid, neopentanoic acid, neoheptanoic acid, neononanoic acid, trimethyl hexanoic acid, neodecanoic acid, and isostearic acid. Examples of suitable fatty acid esters include aliphatic fatty acid esters such as isopropyl n-butyrate, isopropyl n-hexanoate, isopropyl n-decanoate, isopropyl myristate, isopropyl palmitate, and octyldodecyl myristate; alkyl fatty acid esters such as ethyl acetate, butyl acetate, methyl acetate, methylvalerate, methylpropionate, diethyl sebacate, and ethyl oleate; and diisopropyl adipate and dimethyl isosorbide. Examples of suitable polyols include propylene glycol, butylene glycol, polyethylene glycol, ethylene glycol, diethylene glycol, triethylene glycol, dipropylene glycol, ethoxydiglycol, pentylene glycol, glycerol, propanediol, butanediol, pentanediol, hexanetriol, and glycerin. Examples of suitable amides include urea, dimethylacetamide, diethyltoluamide, dimethylformamide (DMF), dimethyloctamide, dimethyldecamide, biodegradable cyclic urea (e.g., 1-alkyl-4-imidazoline-2-one), pyrrolidone derivatives, biodegradable pyrrolidone derivatives (e.g., fatty acid esters of N-(2-hydroxyethyl)-2-pyrrolidone), cyclic amides, hexamethylenelauramide and its derivatives, diethanolamine, and triethanolamine. Examples of pyrrolidone derivatives include 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkylpyrrolidone, and N-methylpyrrolidone. Examples of cyclic amides include 1-dodecylazacycloheptane-2-one (e.g., Azone®), 1-geranylazacycloheptan-2-one, 1-farnesylaz acycloheptan-2-one, 1-geranylgeranylazacycloheptan-2-one, 1-(3,7-dimethyloctyl)azacycloheptan-2-one, 1-(3,7,11-trimethyldodecyl)azacyclohaptane-2-one, 1-geranylazacyclohexane-2-one, 1-geranylazacyclopentan-2,5-dione, and 1-farnesylazacyclopentan-2-one.

Typically, the compositions of the present disclosure include from about 0.01% (by weight of the composition) to about 25% (by weight of the composition) of a skin penetration enhancer, including from about 1% (by weight of the composition) to about 15% (by weight of the composition) of a skin penetration enhancer, and including from about 2% (by weight of the composition) to about 10% (by weight of the composition) of a skin penetration enhancer.

Optionally, the *Undaria* and/or *Bidens*-containing topical compositions may be formulated with a polar co-solvent to increase the permeability of the *Undaria* and *Bidens* into the skin. Preferably, the polar co-solvent is fully miscible in the composition, and has a high affinity for the intercellular spaces in the stratum corneum. Without wishing to be bound by any particular theory, it is believed that polar co-solvents with such characteristics are driven by osmosis into the intercellular spaces in the stratum corneum, causing the stratum corneum to swell. In such a swollen state, the intercellular spaces are more liquid-like and disordered, which enables the *Undaria* and/or *Bidens* extracts to more easily diffuse through the stratum corneum.

Examples of suitable polar co-solvents for inclusion in the compositions of the present disclosure include glycerin, propanediol, ethanol, propylene glycol, butanol, isopropanol, propanol, dimethyl isosorbide, butylene glycol, polyethylene glycol, dipropylene glycol, ethoxydiglycol, pentylene glycol, and combinations thereof.

Typically, the compositions of the present disclosure include from about 1% (by weight of the composition) to about 99% (by weight of the composition) of a polar co-solvent, including from about 1% (by weight of the composition) to about 75% (by weight of the composition) of a polar co-solvent, including from about 1% (by weight of the composition) to about 50% (by weight of the composition) of a polar co-solvent, including from about 1.5% (by weight of the composition) to about 25% (by weight of the composition) of a polar co-solvent, including from about 2% (by weight of the composition) to about 15% (by weight of the composition) of a polar co-solvent, and including from about 2.5% (by weight of the composition) to about 10% (by weight of the composition) of a polar co-solvent.

In some embodiments, the compositions can further include beta-sitosterol. Suitable amounts of beta-sitosterol can be from about 0.001% by weight of the composition to about 10.0% by weight of the composition. More typically, the amount of beta-sitosterol can be from about 0.005% by weight of the composition to about 7.5% by weight of the composition. Even more suitable, the amount of beta-sitosterol can be from about 0.01% by weight of the composition to about 5.0% by weight of the composition.

The composition can further include other known collagen, elastin, and extracellular matrix-stimulating ingredients. Collagen is a protein found in the connective tissue of the skin and other tissues of the body. Suitable collagen enhancers can be, for example, vitamins such as ascorbic acid and derivatives thereof, peptides such as palmitoyl tripeptide-5, botanical extracts such as pomegranate or mushroom, and minerals such as hematite.

Elastin is a protein found in the connective tissue of the skin and other tissues of the body. Suitable elastin enhancers can be, for example, vitamins such as ascorbic acid and derivatives thereof, peptides such palmitoyl hexapeptide-12, botanical extracts such as kudzu, horsetail, rice, dill and rosemary, and minerals such as zinc and copper.

The compositions can further include a vasodilator. Vasodilators can increase the blood flow within the skin. Suitable vasodilators can be, for example, glyceryl trinitrate, resveratrol, caffeine, ginger extract, *ginseng* and other botanical extracts such as, for example, hawthorn, mint, ivy, coffee and tea.

The compositions can further include a skin soothing agent. As used herein, "skin soothing agent" refers to compounds that reduce or prevent skin irritation. Skin irritation can result from loss of moisture, a change in pH, sweat, contact dermatitis from perfumes, powders, laundry detergent from clothing, and other compounds. Skin soothing agents can reduce irritation by neutralizing an irritant, down-regulating inflammatory cascades in the skin, and/or providing a protective layer on the skin. Suitable skin soothing agents can be, for example, botanical extracts such as calendula, chamomile, aloe, comfrey, coneflower; active materials such as allantoin, bisabolol, panthenol, beta-glucan, colloidal oatmeal, and ingredient blends such as SYMCALMIN (INCI: butylene glycol, pentylene glycol, hydroxyphenyl propamidobenzoic acid; commercially available from Symrise (Holzmiden, Germany) and SEPI- CALM (INCI: sodium palmitoyl proline, nymphaea alba flower extract; commercially available from Seppic (Fairfield, N.J.).

The compositions can further include a humectant. Humectants can elevate the hydration of the skin, in particular the epidermis and the dermis. Suitable humectants can be, for example, glycerol, glycerin, lactic acid, urea, aloe vera, betaine, hyaluronic acid, propanediol, propylene glycol, butylene glycol, and combinations thereof.

The compositions can further include an emulsifier, and in particular, an emulsifier that creates liquid crystalline networks or liposomal networks. Suitable non-limiting exemplary emulsifiers include, for example, OLIVEMO 1000 (INCI: Cetearyl Olivate (and) Sorbitan Olivate; commercially available from HallStar Company (Chicago, Ill.)), Arlacel™ LC (INCI: Sorbitan Stearate (and) Sorbityl Laurate; commercially available from Croda (Edison, N.J.), CRYSTALCAST® MM (INCI: Beta Sitosterol (and) Sucrose Stearate (and) Sucrose Distearate (and) Cetyl Alcohol (and) Stearyl Alcohol; commercially available from MMP Inc. (South Plainfield, N.J.), UNIOX CRISTAL (INCI: Cetearyl Alcohol (and) Polysorbate 60 (and) Cetearyl Glucoside; commercially available from Chemyunion (Sao Paulo, Brazil). Other suitable emulsifiers include lecithin, hydrogenated lecithin, lysolecithin, phosphatidylcholine, phospholipids, and combinations thereof.

The compositions can further include a preservative to preserve the stability. Preservatives can also prevent the growth of microbial organisms in the compositions. Suitable preservatives are known in the art, and include, for example, methylparaben, phenoxyethanol, capryl glycol, glyceryl caprylate, benzoic acid, sorbic acid, gallic acid, propylparaben and combinations thereof.

The compositions can further include a pH adjuster to control/maintain the pH of the composition within the range of skin pH. A suitable pH range of the composition can be from about 3.5 to about 6.

The compositions can further include fragrances, scents, dyes, surfactants, rheology modifiers, film formers and other components known to be useful in personal care formulations.

Methods of Use

In another aspect, the present disclosure is directed to methods of using the compositions to reduce skin aging of an individual's face and body.

Thus, in one aspect, the present disclosure is directed to a method for reducing oxidative stress of cells, and in particular dermal fibroblasts and epidermal keratinocytes, thereby reducing signs of skin aging of the face and body in an individual in need thereof. As used herein, "skin aging" refers to increased skin wrinkling, increased appearance of fine lines, thinning skin, sagging skin, skin dryness, and skin itchiness. Oxidative stress of cells alters the equilibrium between cellular death and cellular proliferation, and further, can impair tissue regeneration. Typically, oxidative stress is a result of the overproduction of reactive oxygen species (ROS), which causes damage to the inner and outer mitochondrial membranes and opens the mitochondrial permeability transition pores, thereby inducing apoptosis. The method includes topically applying a composition including an *Undaria* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In another aspect, the present disclosure is directed to a method for reducing oxidative stress-induced apoptosis of cells, and in particular dermal fibroblasts and epidermal keratinocytes, in an individual in need thereof. The method includes topically applying a composition including an *Undaria* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In yet another aspect, the present disclosure is directed to a method for reducing photodamage of cells, and in particular dermal fibroblasts and epidermal keratinocytes, in an individual in need thereof. As used herein, "photodamage" refers to the damage caused to skin, and in particular, dermal fibroblasts, as a result of exposure to UV irradiation. The method includes topically applying a composition including an *Undaria* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In yet another aspect, the present disclosure is directed to a method for maintaining the cellular reduced glutathione concentration of cells, and in particular dermal fibroblasts and epidermal keratinocytes, in an individual in need thereof. Particularly, the methods are directed to maintaining cellular reduced glutathione concentration of dermal fibroblasts under oxidative stress and/or UV irradiation conditions. The methods include topically applying a composition that comprises an *Undaria* extract and a hydrophilic carrier to a target skin region of the individual. The target skin region can be, for example, facial skin, neck skin, breast skin, shoulder skin, chest skin, leg skin, hand skin, feet skin, vulvar skin, for example, the vulva, labia, labia majora, labia minor, mons pubis, and vulval vestibule, and combinations thereof.

In yet other embodiments of the present disclosure, the methods include topically applying a composition including a *Bidens* extract to a target skin region of the individual to reduce oxidative stress of cells, and in particular dermal fibroblasts and epidermal keratinocytes. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In another aspect, the present disclosure is directed to a method for reducing oxidative stress-induced apoptosis of cells, and in particular dermal fibroblasts and epidermal keratinocytes, in an individual in need thereof. The method includes topically applying a composition including a *Bidens* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In yet another aspect, the present disclosure is directed to a method for reducing photodamage of cells, and in particular dermal fibroblasts and epidermal keratinocytes, in an individual in need thereof. The method includes topically applying a composition including a *Bidens* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In yet another aspect, the present disclosure is directed to a method for maintaining the cellular reduced glutathione concentration of cells, and in particular dermal fibroblasts and epidermal keratinocytes, in an individual in need thereof. Particularly, the methods are directed to maintaining cellular reduced glutathione concentration of dermal fibroblasts under oxidative stress and/or UV irradiation conditions. The methods include topically applying a composition that comprises a *Bidens* extract and a hydrophilic carrier to a target skin region of the individual. The target skin region can be, for example, facial skin, neck skin, breast skin, shoulder skin, chest skin, leg skin, hand skin, feet skin, vulvar skin, for example, the vulva, labia, labia majora, labia minor, mons pubis, and vulval vestibule, and combinations thereof.

As used herein, an "individual in need" refers to an individual showing increased visible signs of skin aging such as, for example, wrinkles, fine lines, thinning skin, sagging skin, skin dryness, skin itchiness, skin fragility, skin tears, loss in skin tone, loss in skin fullness, loss in skin plumpness, and combinations thereof, due to extrinsic conditions, and in particular, oxidative stress and/or photodamage of cells, and in particular, dermal fibroblasts and epidermal keratinocytes. In some embodiments, the individual in need is an individual in which the cellular glutathione concentration of dermal fibroblasts has decreased as a result of oxidative stress and/or UV irradiation. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein.

As used herein, the term "individual" refers to a male human or a female human. In certain embodiments, the individual is a postmenopausal female human.

The compositions used in the methods described herein can further include additional ingredients as described herein and other components known to be useful in personal care formulations.

The composition can be applied to the target skin region by any suitable delivery vehicle. For example, the composition can be applied as a lotion, as a wash, as a gel, as a salve, as an ointment, as a cream, as a solid stick and as a foam. Additionally, the composition can be applied with a wipe, with mitts and gloves, using an aerosol dispenser, using a pump spray, using a trigger spray and using a squeeze bottle.

The compositions can be applied daily, every other day, every couple of days, every week, every month, and every year, as desired. The compositions can be applied multiple times per day, multiple times per week and/or multiple times per month.

In some embodiments, the compositions of the present disclosure can be used with additional skin care compositions as part of a skin care regimen. For example, in facial treatment and care, users typically use multiple products for cleansing, toning, and treating the skin of the face. Accordingly, the first product comprises a first composition typically capable of providing a first benefit to a user, and the second product comprises a second composition typically capable of providing a second benefit to a user. In the present disclosure, it should be understood that at least one of the products of the regime includes the topical composition of the present disclosure, thereby providing the benefit of enhancing the cellular response to oxidative stress and/or photodamage. In some embodiments, it should be understood by one skilled in the art, that while the first product and second product can independently provide any benefit known in the art of the particular care regimen, in each particular multi-product care regimen, the first product and second product may include different compositions and thus, provide different benefits to the user.

Furthermore, as with the first product and second product of the care regimen, if more than two products are used in the multi-product care regimen, such as third, fourth, and/or fifth products (and more products if more than five products are desired), it should be recognized that the additional products should include active ingredients, each independently being capable of providing additional benefits to a user.

In an alternative embodiment, the multi-product care regime can include more than two products and can be configured such to provide a multiple day regimen. Without being limiting, in one example, the multi-product care regimen provides skin care for multiple days and, as such, a first product includes, for example, a cleansing composition, a second product includes the anti-skin aging composition of the present disclosure, a third product includes the same cleansing composition as the first product, and a fourth product includes the same anti-skin aging composition as the second product.

Without being limiting, examples of additional compositions providing skin care benefits in addition to the anti-skin aging composition of the present disclosure can include compositions for cleansing, toning, treating, moisturizing, protecting, finishing, and the like.

When the additional composition is a cleansing composition, the cleansing composition may be in any form known in the art, such as, for example, hand soaps, body soaps, body washes, shampoos, surface cleaners, dish soaps, facial cleansers, hand washes, and the like. These types of cleansing compositions typically include at least one foaming agent, such as a surfactant. Although discussed herein primarily in terms of a surfactant, it should be understood that the cleansing compositions may comprise other cleansing agents, and need not comprise a surfactant. For example, in certain embodiments, the compositions may comprise a thickener, a swellable clay, a foaming agent (which may or may not comprise a surfactant (e.g., ethoxylated skin conditioning agents, solubilizers, and derivatized silicone polymers)), and optionally a solvent or other carrier. Examples of such compositions include, for example, lotions, creams, anti-microbial compositions, and the like.

Suitable surfactants for use in the cleansing composition include anionic surfactants, amphoteric surfactants, cationic surfactants, zwitterionic surfactants, non-ionic surfactants, and combinations thereof.

Suitable anionic surfactants include, for example, alkyl sulfates, alkyl ether sulfates, alkyl aryl sulfonates, alphaolefin sulfonates, alkali metal or ammonium salts of alkyl sulfates, alkali metal or ammonium salts of alkyl ether sulfates, alkyl phosphates, silicone phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, sulphosuccinates (e.g., sodium dioctylsulphosuccinate), and combinations thereof. Specific examples of anionic surfactants include sodium lauryl sulphate, sodium lauryl ether sulphate, ammonium lauryl sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl sulphate, sodium N-lauryl sarcosinate, and combinations thereof.

Suitable cationic surfactants include, for example, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include behenyltrimonium chloride, stearlkonium chloride, distearalkonium chloride, chlorohexidine diglutamate, polyhexamethylene biguanide (PHMB), cetyl pyridinium chloride, benzammonium chloride, benzalkonium chloride, and combinations thereof.

Suitable amphoteric surfactants include, for example, betaines, alkylamido betaines, sulfobetaines, N-alkyl betaines, sultaines, amphoacetates, amophodiacetates, imidazoline carboxylates, sarcosinates, acylamphoglycinates, such as cocamphocarboxyglycinates and acylamphopropionates, and combinations thereof. Specific examples of amphoteric surfactants include cocamidopropyl betaine, lauramidopropyl betaine, meadowfoamamidopropyl betaine, sodium cocoyl sarcosinate, sodium cocamphoacetate, disodium cocoamphodiacetate, ammonium cocoyl sarcosinate, sodium cocoamphopropionate, and combinations thereof.

Suitable zwitterionic surfactants include, for example, alkyl amine oxides, silicone amine oxides, and combinations thereof. Specific examples of suitable zwitterionic surfactants include, for example, 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Suitable non-ionic surfactants include, for example, mono- and di-alkanolamides such as, for example, cocamide MEA and cocamide DEA, amine oxides, alkyl polyglucosides, ethoxylated silicones, ethoxylated alcohols, ethoxylated carboxylic acids, ethoxylated amines, ethoxylated amides, ethoxylated alkylolamides, ethoxylated alkylphenols, ethoxylated glyceryl esters, ethoxylated sorbitan esters, ethoxylated phosphate esters, glycol stearate, glyceryl stearate, and combinations thereof. It will be recognized by one skilled in the art that many of the nonionic surfactants described herein may act to improve the foaming properties of the cleansing composition of the multi-product care system, and may provide a more compact, reduced bubble size or creamy foam.

The cleansing composition may also include a thickener, which acts to thicken or increase the viscosity of the cleansing formulation. A variety of thickeners may be used in the cleansing compositions described herein. In one embodiment, the thickener may be a cellulosic thickener or gum. Examples of suitable cellulosic or gum thickeners include xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, hydroxypropylcellulose, hydroyethylcellulose, propylene glycol alginate, hydroxypropyl guar, amylopectin, cellulose gum, chitosan, modified chitosan, hydroxypropyl methylcellulose, microcrystalline cellulose, silica, fumed silica, colloidal silica, dehydroxanthan gum, non-acrylic based carbomers, and combinations thereof.

Alternately or in addition, the thickener may be an acrylic based polymer. Non-limiting examples of suitable acrylic based polymer thickeners include acrylates/C10-C30 alkyl acrylate crosspolymers, certain carbomers, acrylates copolymers, aminoacrylates copolymers, and combinations thereof. Examples of commercially available acrylic based polymer thickeners include Structure® Plus (Akzo Nobel, Pasadena, Calif.), which is an acrylates/aminoacrylates/C10-30 alkyl PEG-20 itaconate copolymer, Carbopol® Aqua SF-1 Polymer (Lubrizol Advanced Materials, Cleveland, Ohio), which is an acrylates copolymer, PEMULENO TR-1 and TR-2 and Carbopol® ETD 2020 (available from Lubrizol Advanced Materials), which are acrylates/C10-30 alkyl acrylates crosspolymers, and the Carbopol® Ultrez series of polymers (available from Lubrizol Advanced Materials), which are carbomers.

Additional suitable agents for use in the cleansing composition may include humectants, preservatives, fragrances, chelating agents, and combinations thereof.

A skin care regime may further include a toning composition. Toning compositions provide such benefits as closing pores of a user's skin, restoring the natural pH of the skin (typically, a pH of from about 5.0 to about 5.5), removing skin impurities (e.g., dirt, oils, sebum, make-up, pollutants, and the like), hydrating the skin, and generally preparing the skin for treatment using a treatment composition, such as the anti-aging composition of the present disclosure, and/or an additional treatment composition as described below.

Generally, toning compositions for skin care include astringents, humectants, carriers, and combinations thereof. Suitable astringents include, for example, ethanol, witch hazel, rose water, alum, oatmeal, yarrow, bayberry, cold water, rubbing alcohol, astringent preparations such as silver nitrate, zinc oxide, zinc sulfate, Burow's solution, tincture of benzoin, and vegetable substances such as tannic and gallic acid, and combinations thereof. As used herein, the term "cold water" refers to water having a temperature below room temperature (approximately 25° C. (77° F.)).

Suitable humectants include, for example, glycerin, glycerin derivatives, sodium hyaluronate, betaine, amino acids, glycosaminoglycans, honey, sorbitol, glycols, polyols, sugars, hydrogenated starch hydrolysates, salts of PCA, lactic acid, lactates, and urea. A particularly preferred humectant is glycerin.

Carriers for the toning compositions can be any carrier material typically known in the cosmetic and medical arts as a basis for ointments, lotions, creams, salves, aerosols, gels, suspensions, sprays, foams, and the like, and may be used in their art-established levels. In one particular embodiment, the carrier is an aqueous carrier. In another embodiment, the carrier is an alcohol carrier. The alcohol carrier can be any suitable alcohol. One particularly preferred alcohol is ethanol.

Other suitable carriers can also be used in the toning compositions. In certain embodiments, the carriers themselves can provide the skin care benefit. Non-limiting examples of suitable carriers include emollients, sterols or sterol derivatives, natural and synthetic fats or oils, polyols, surfactants, esters, silicones, and other pharmaceutically acceptable carrier materials.

In some embodiments, the skin care regimen includes a treatment composition for treating the skin in addition to benefits provided by the composition of the present disclosure. Exemplary actives for the additional treatment composition may include actives that are known to have a treating effect on the skin such as improving the evenness of skin tone and reduction of acne. More specifically, the treatment agent can be selected from the group consisting of appearance modifying agents (e.g., exfoliating agents, skin-firming agents, anti-callous agents, anti-acne agents, wound care agents, enzyme agents, scar repair agents, humectant agents), therapeutic agents, pharmaceuticals (e.g., drugs, anti-oxidants, transdermal drug delivery agents, botanical extracts, vitamins, magnets, magnetic metals, and foods), xenobiotics, skin coloration agents (e.g., tanning agents, lightening agents, and brightening agents, shine control agents and drugs), shine control agents, colorant agents, surface conditioning agents (e.g., pH adjusting agents, moisturizers, skin conditioners, exfoliation agents, shaving lubricants, anti-callous agents, anti-acne agents, anti-aging agents, wound care agents, skin lipids, enzymes, scar care agents, humectants, powders, botanical extracts, and drugs) external analgesic agents, anti-inflammatory (e.g., anti-irritant agents, anti-allergy agents, wound care agents, transdermal drug delivery, and drugs), fragrances, odor neutralizing agents, soothing agents, calming agents, botanical extracts (e.g., peppermint oil, eucalyptol, eucalyptus oil, camphor, and tea tree oil), peptides, natural and synthetic fats or oils, moisture absorbers, and combinations thereof.

In one embodiment, in addition to the compositions described above, the skin care regimen includes a finishing composition. As with the other compositions, it should be understood that the various active ingredients described herein can be used in any of the products of the multi-product care regimen without departing from the scope of the disclosure.

When included, a finishing composition comprises a finishing agent that typically delivers moisturization, skin protection, or a moisture-barrier for sealing in moisture to the user. Specifically, the finishing agent can be any moisturizing agent, skin protectant, and/or moisture-barrier enhancing agent known in the art.

Additionally, the finishing agent may be capable of providing aesthetic benefits such as skin smoothing or a powdery feel. Examples of additional suitable finishing agents include skin conditioning agents (e.g., pH adjusting agents, moisturizers, skin conditioners, exfoliation agents, shaving lubricants, skin-firming agents, anti-callous agents, anti-acne agents, anti-aging agents, anti-wrinkle agents, anti-dandruff agents, wound care agents, skin lipids, enzymes, scar care agents, humectants, powders, botanical extracts, and drugs), fragrances, botanical extracts, powders, and combinations thereof.

It should be understood that the various active ingredients can be used in any of the products of the multi-product care regimen without departing from the scope of the disclosure. The specific active ingredients of the various products will depend upon the end daily regimen desired.

It should be understood by a skilled artisan that, while skin care systems will be discussed herein, regimes using the compositions of the present disclosure can be used for various other daily regimens comprising steps to cleanse, treat, moisturize and protect the skin. It is understood that skin care regimens can combine all of these steps, some of these steps, or have multiple iterations of the same steps so as to provide desired benefits to the skin.

This written description uses examples to disclose the invention, including the best mode, and also to enable any person skilled in the art to practice the invention, including making and using the compositions and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The disclosure will be more fully understood upon consideration of the following non-limiting Examples.

EXAMPLE 1

Cell Viability

In this Example, a cell viability test was conducted to test cytotoxicity.

Primary human dermal fibroblasts were grown to confluence in growth media (DMEM+10% FBS) at 37° C. in 5% $CO_2$ atmosphere. Samples of cells (n=3) were then treated with increasing concentrations of UNDARINE™ or ECO-BIDENS™ in growth media (DMEM (Life Technologies, Grand Island, N.Y.) +2% Fetal Bovine Serum (FBS) (Life Technologies)+1×antibiotic/antimycotic (AA)) for either 1 or 24 hours. After the treatment, cells were washed twice in PBS, let recover in growth media (DMEM+10% FBS) for 12 hours at 37° C. in 5% $CO_2$ atmosphere, and then incubated with ALAMARBLUE® (Life Technologies, Grand Island, N.Y.) for 2 hours at 37° C. in 5% $CO_2$ atmosphere. The ALAMARBLUE® assay incorporates a fluorometric/colorimetric growth indicator based on detection of metabolic activity. Specifically, the system incorporates an oxidation-reduction (REDOX) indicator that both fluoresces and changes color in response to chemical reduction of growth medium resulting from cell growth.

The mitochondrial uncoupling drug, Carbonyl cyanide 3-chlorophenylhydrazone (CCCP) (commercially available from Sigma-Aldrich, St. Louis, Mo.), was utilized as a positive control for cytotoxicity. Further, non-treated samples of cells were utilized as a negative control.

The intensities of fluorescent emission were recorded using SpectraMax® M5 (Molecular Devices, Sunnyvale, Calif.) at 585 nm. Viability was determined as follows:

Viability (%)=((fluorescence intensity at 585 nm of the treated sample)/(fluorescence intensity at 585 nm of the non-treated sample))×100.

As demonstrated in FIG. 1, neither of the tested active agents significantly reduced cellular viability at concentrations of 1% or 3%.

EXAMPLE 2

In this Example, an *Undaria* extract was analyzed for its ability to protect fibroblasts against oxidative stress.

Primary fibroblasts from an abdominal explant of a 51-year old woman were grown to confluence in growth media (DMEM+10% FBS+1× antibiotic/antimycotic (AA)) and then treated for 20 hours with 3% v/v UNDARINE™ in growth media (DMEM (Life Technologies, Grand Island, N.Y.)+2% Fetal Bovine Serum (FBS) (Life Technologies)+1×antibiotic/antimycotic (AA)). Cells were washed and then a sample of cells (n=4) was further treated with 200 μM $H_2O_2$ for 1 hour at 37° C. A second sample of cells (n=4) was not treated with UNDARINE™, but was treated with $H_2O_2$. After removing $H_2O_2$, cells were allowed to recover in media at 37° C. in 5% $CO_2$ atmosphere. A sample of untreated cells (n=4) was used as a control. After 12 hours, cells were incubated in PBS+10% ALAMARBLUE® (Life Technologies, Grand Island, N.Y.) for 1 hour at 37° C. in 5% $CO_2$ and fluorescence emission was measured using SpectraMax® M5 (Molecular Devices, Sunnyvale, Calif.) (560EX nm/590 nm). The results are shown in FIG. 2.

Figure 2:
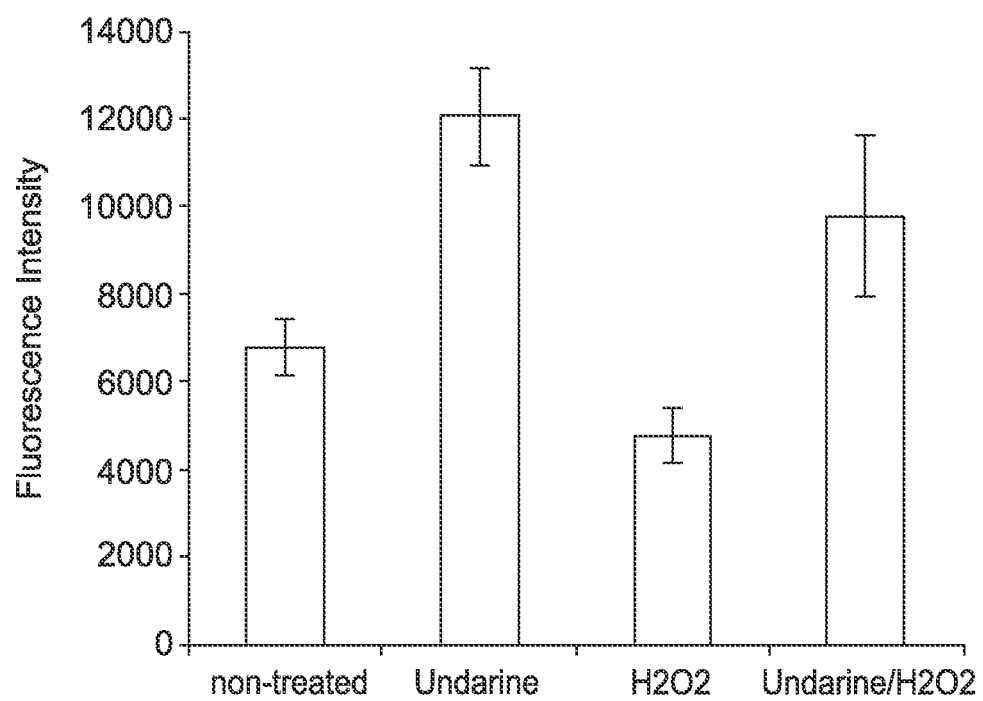
FIG. 2 is a graph depicting fluorescence emission as an indicator of oxidative stress as analyzed in Example 2.
Figure 3A:
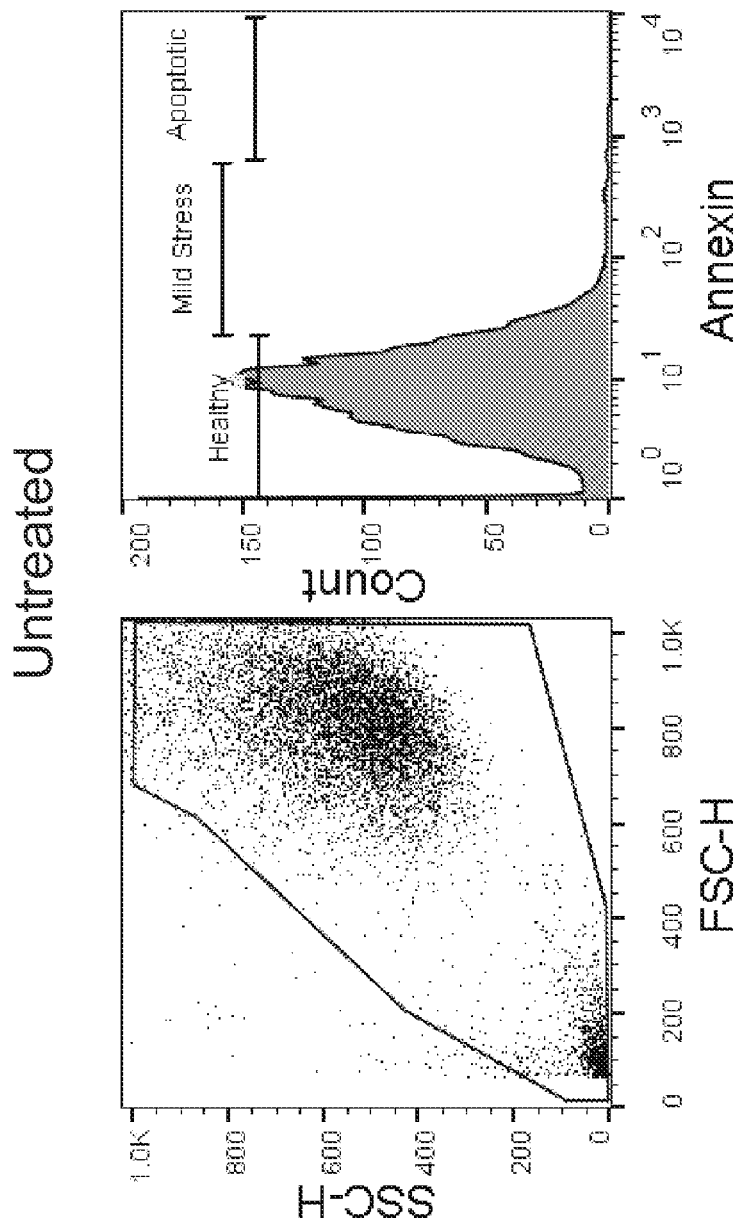
FIGS. 3A-3D are flow cytometer readings of Side Scatter (SSC) and Forward Scatter (FSC) as measured in Example 3.
Figure 3B:
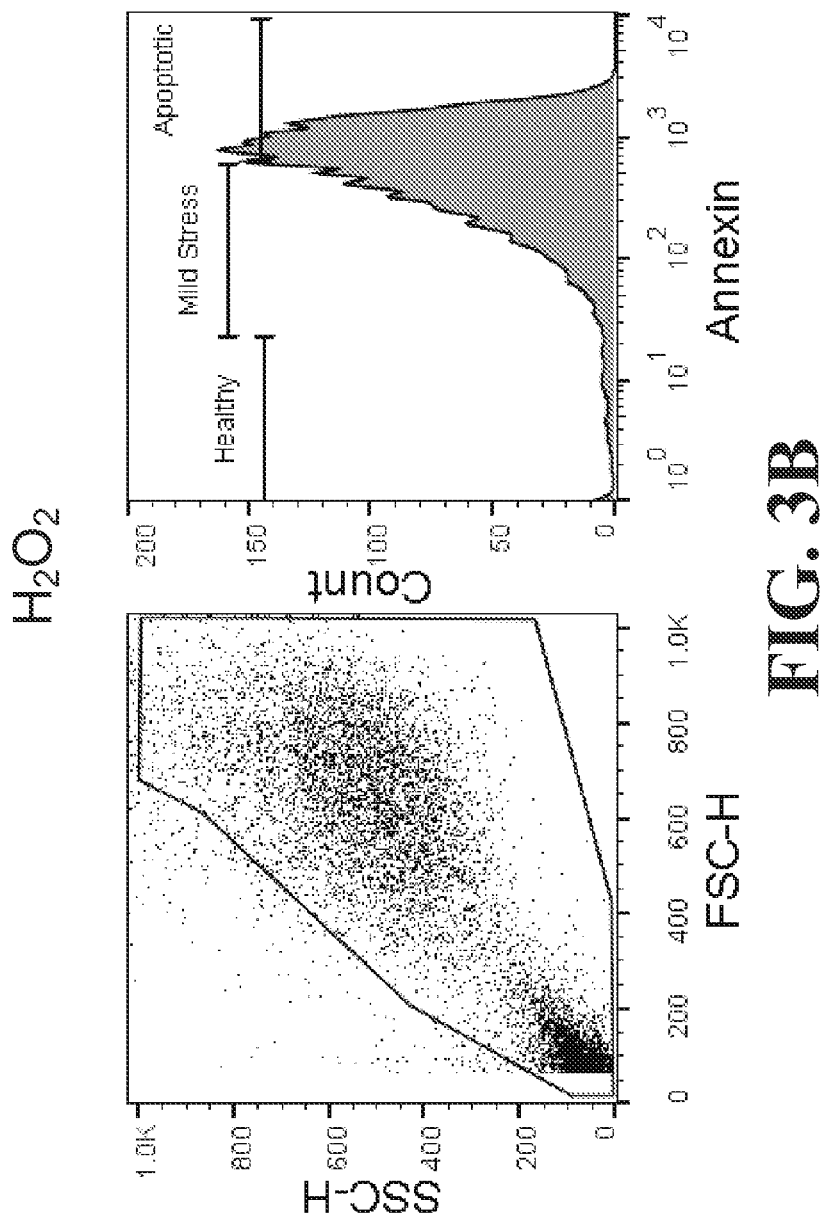
Figure 3C:
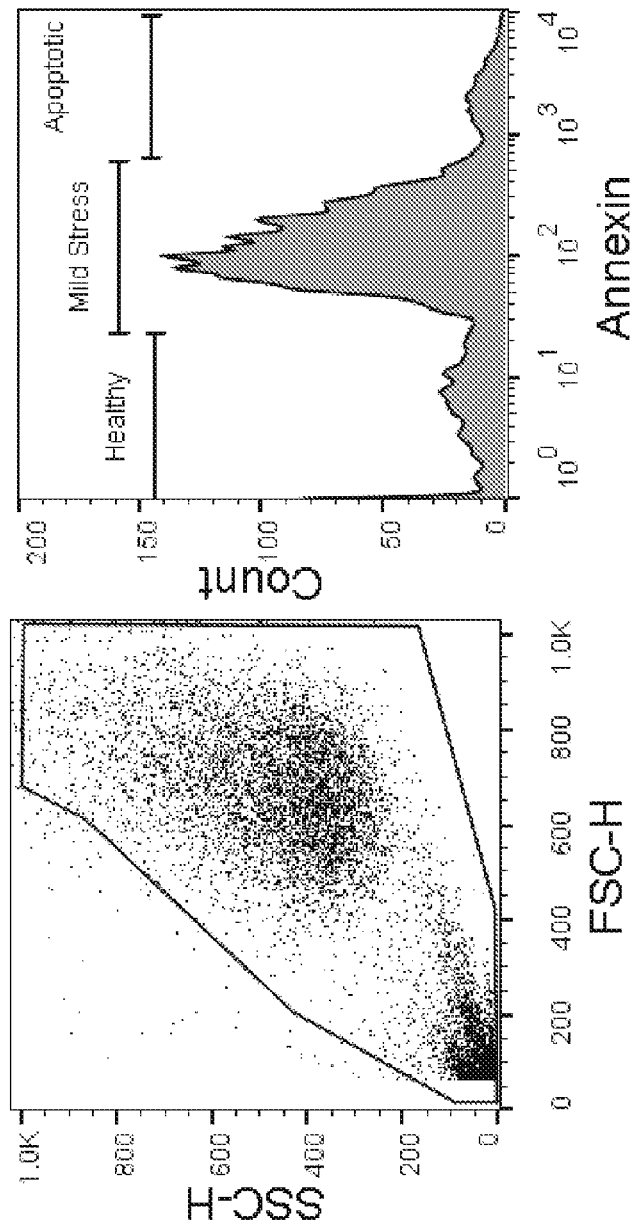
Figure 3D:
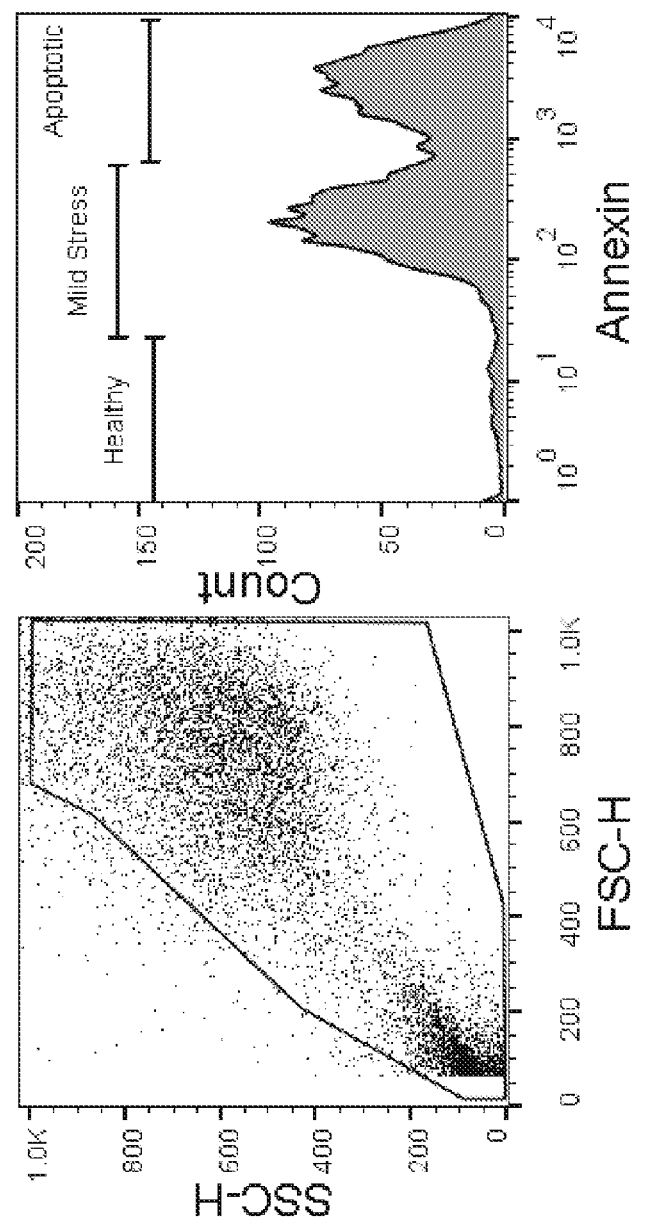

As shown in FIG. 2, UNDARINE™ protected the cells from $H_2O_2$ exposure.

EXAMPLE 3

In this Example, an *Undaria* extract was analyzed for its ability to protect fibroblasts against $H_2O_2$-induced apoptosis.

Human dermal fibroblasts were grown to confluence in growth media (DMEM+10% FBS) and then treated for 12 hours with 3% v/v UNDARINE™ in growth media (DMEM (Life Technologies, Grand Island, N.Y.)+2% Fetal Bovine Serum (FBS) (Life Technologies)+1×antibiotic/antimycotic (AA)). Cells were washed twice with PBS and then a sample of cells (n=4) was further treated with 200 μM $H_2O_2$ for 1 hour at 37° C. A second sample of cells (n=4) was not treated with UNDARINE™, but was treated with $H_2O_2$. A sample of untreated cells (n=4) was used as a control. After further washing with PBS, cells were allowed to recover in media at 37° C. in 5% $CO_2$ atmosphere. After 12 hours, cells were stained with the apoptotic marker Annexin V Alexa Fluor 488 (Life Technologies, Grand Island, N.Y.) (fluorescent emission reported as Annexin). Annexin V is used as an industry standard as a marker of early apoptosis. Particularly, compositions and/or compounds that reduce its expression would be considered highly favorable/effective at improving skin function and appearance. The results are shown in FIGS. 3A-3D.

As shown in FIGS. 3A-3D, UNDARINE™ prevented the increase in an early apoptotic marker caused by the $H_2O_2$ insults. Also, FSC and HSC values (size and granularity) indicated a decrease in percentage of apoptotic cells in UNDARINET™-treated samples.

EXAMPLE 4

In this Example, the effect of a *Bidens* extract on $H_2O_2$ or UV-induced photodamage in human dermal fibroblasts was analyzed.

Primary fibroblasts were isolated from an abdominal skin explant of a 32-year old Caucasian female. The fibroblasts were cultured at 37° C. in 5% $CO_2$ atmosphere in 24-well plates including growth media (DMEM (Life Technologies, Grand Island, N.Y.)+2% Fetal Bovine Serum (FBS) (Life Technologies)+1×antibiotic/antimycotic (AA)) up to 100% confluence.

After culturing to 100% confluence, the cells were treated for 20 hours with 3% v/v ECOBIDENS™ in growth media. The cells were then washed twice with PBS, and either treated with 200 μM $H_2O_2$ (n=4) in growth media for one hour at 37° C. in 5% $CO_2$ atmosphere or submerged in 0.5 ml of PBS and exposed to 100 mJ UV/cm² (n=4).

Figure 4:
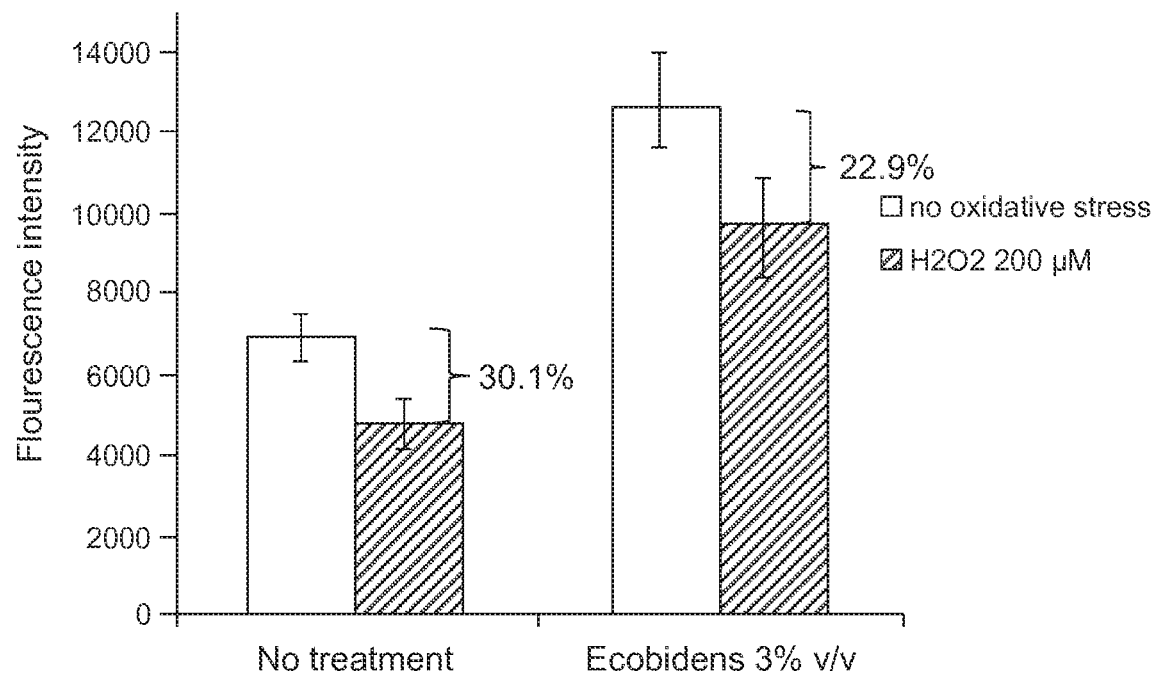
FIG. 4 is a graph depicting fluorescence emission as an indicator of oxidative stress as analyzed in Example 4.
Figure 5:
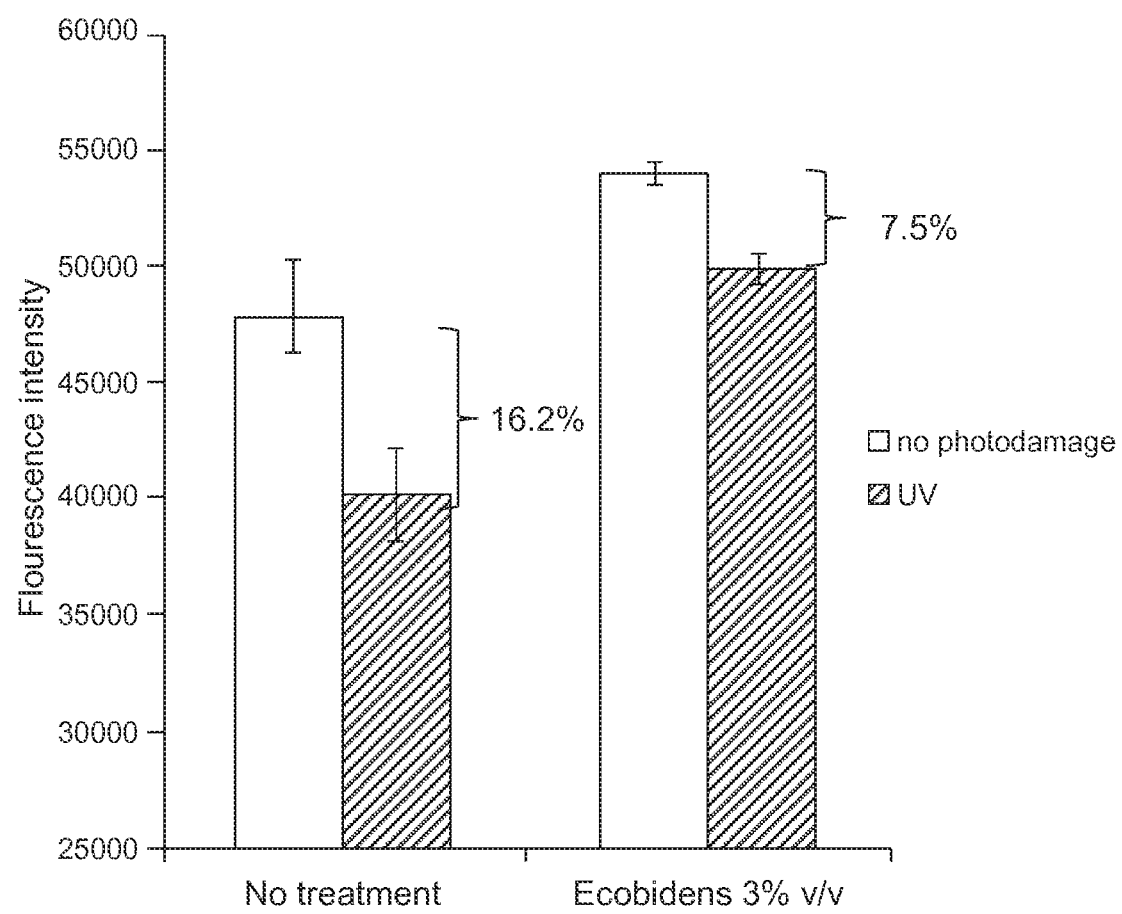
FIG. 5 is a graph depicting fluorescence emission as an indicator of UV photodamage as analyzed in Example 4.
Figure 6A:
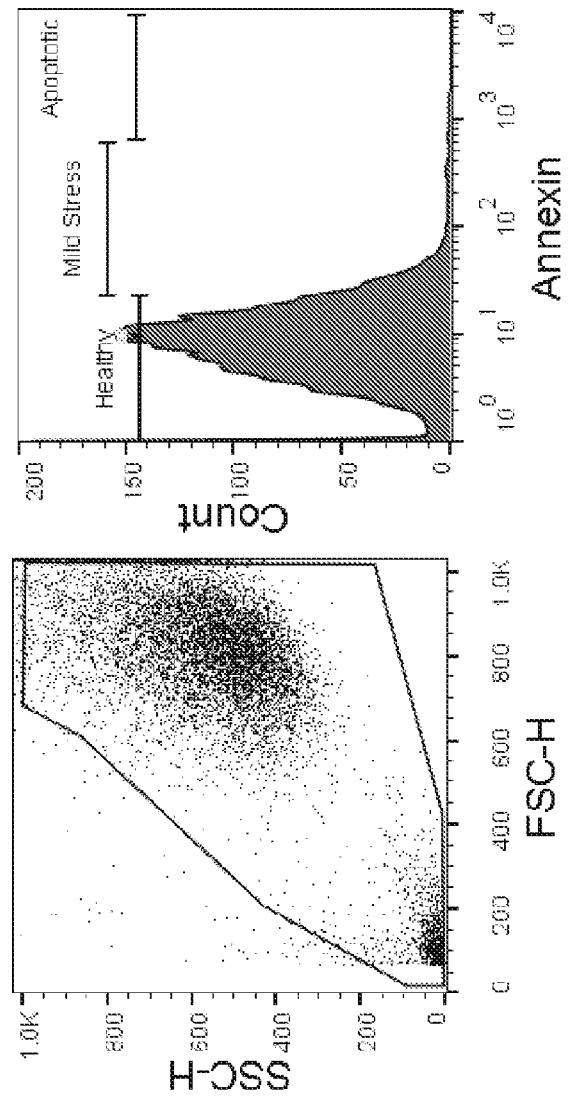
FIGS. 6A-6F are flow cytometer readings of Side Scatter (SSC) and Forward Scatter (FSC) as measured in Example 5.
Figure 6B:
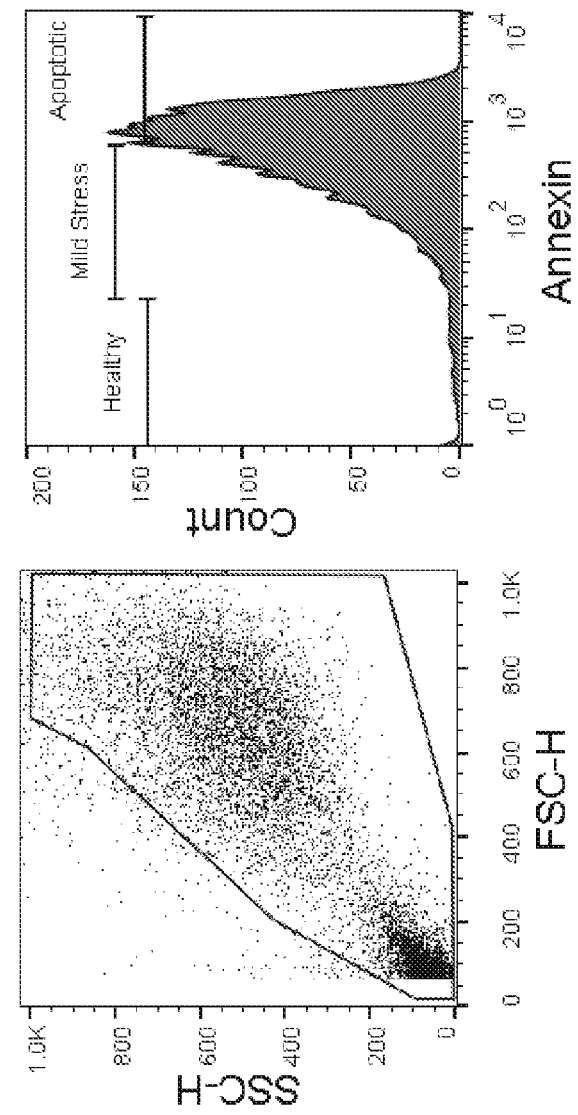
Figure 6C:
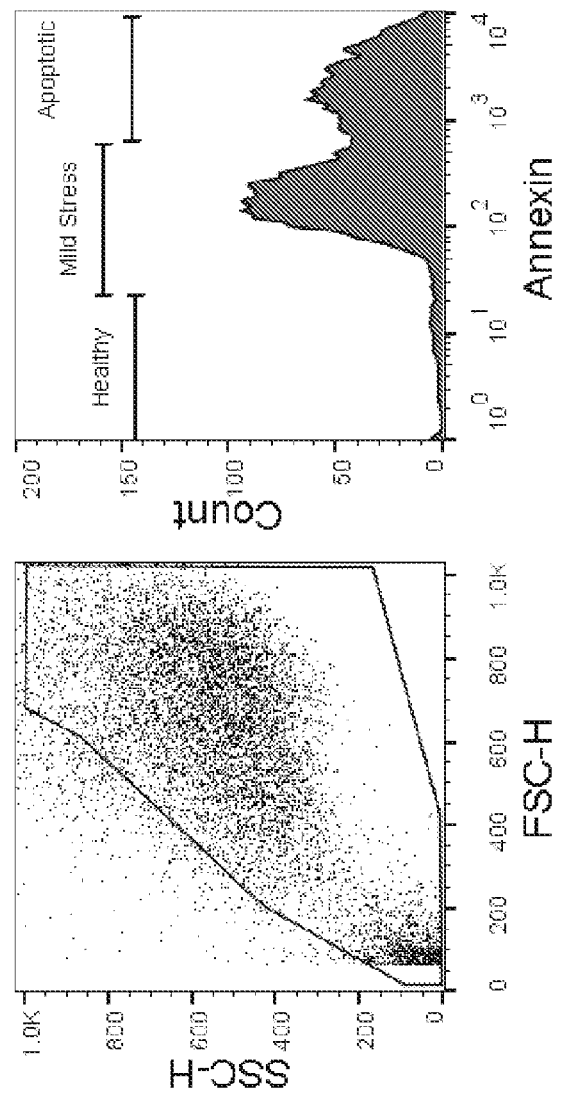
Figure 6D:
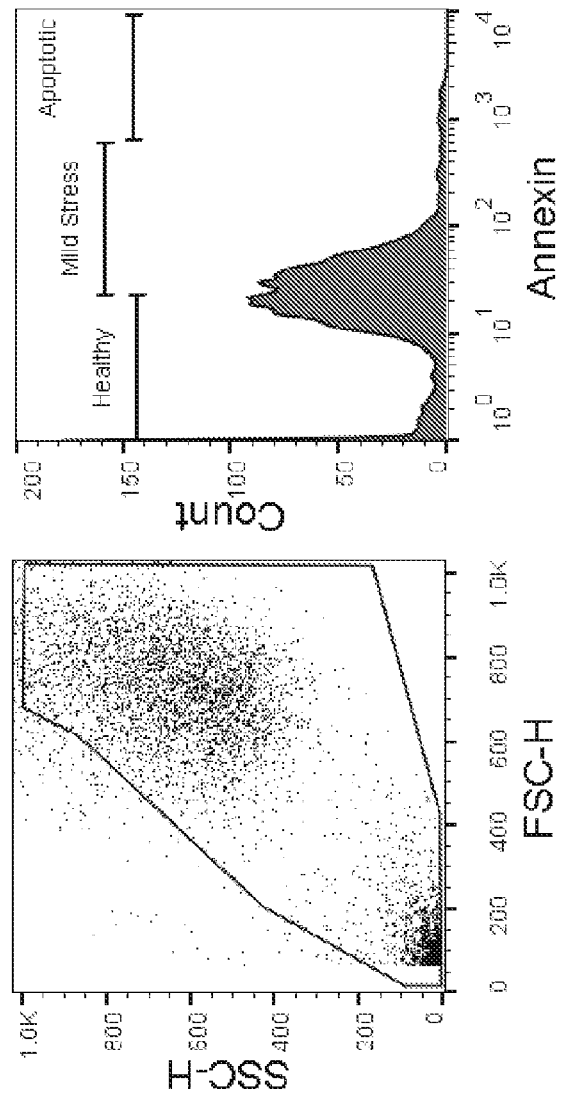
Figure 6E:
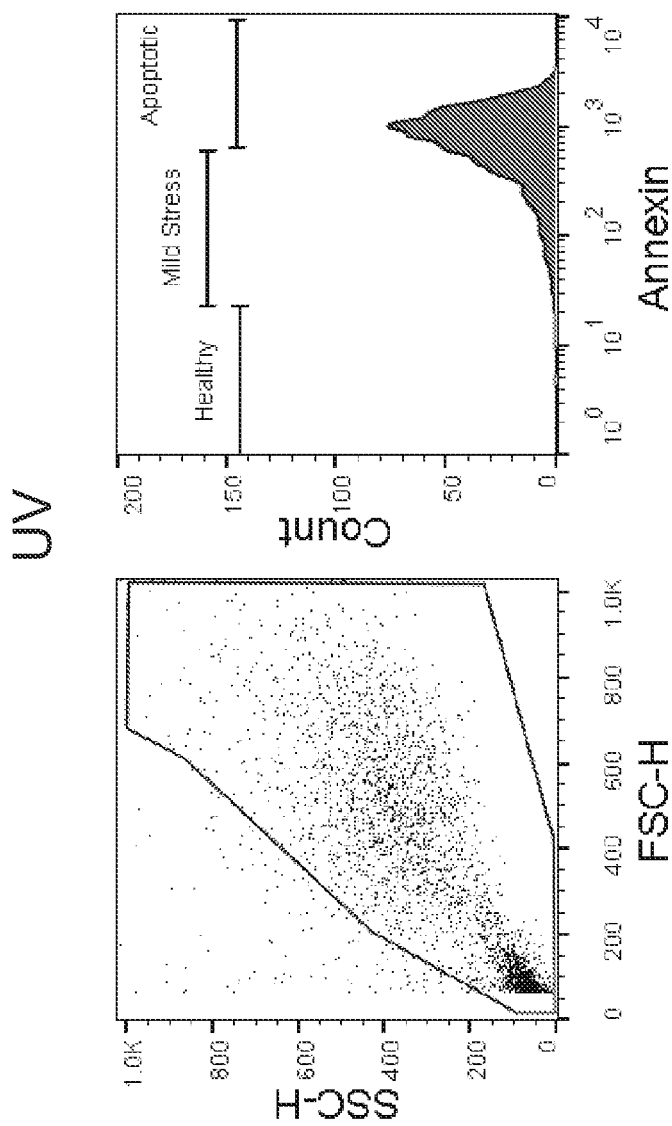
Figure 6F:
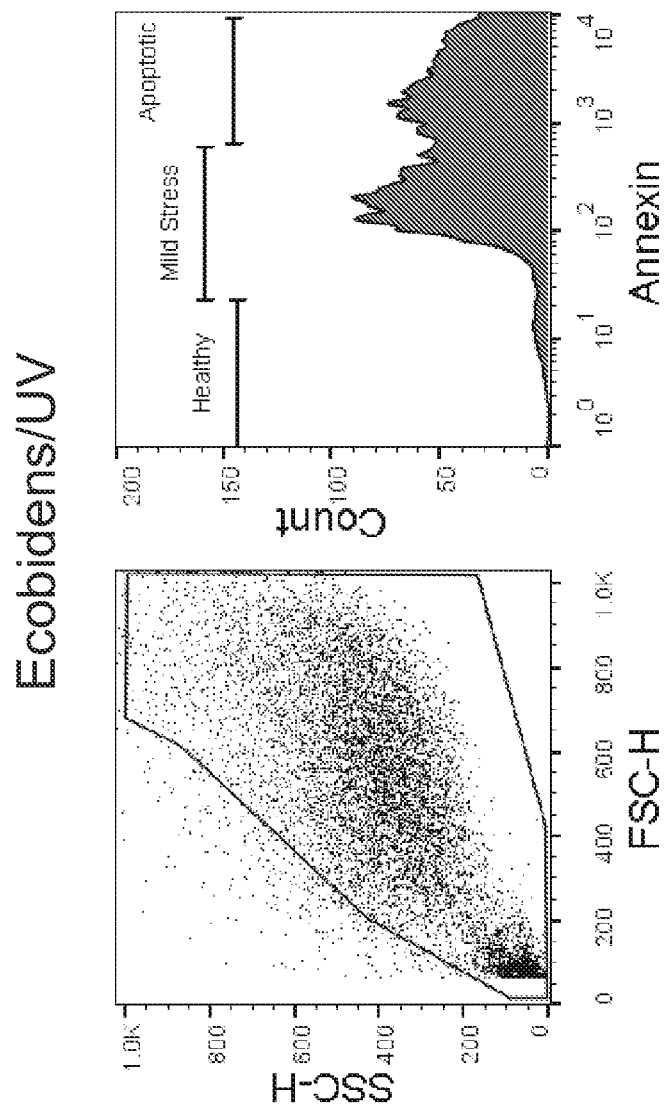

After washing twice with PBS, the cells were then left to recover for approximately 12 hours in media at 37° C. in 5% $CO_2$ atmosphere. The media was then collected and stored at −80° C. for further cytokine analysis and it was replaced with PBS+10% ALAMARBLUE® (Life Technologies). After incubating for one hour at 37° C. in 5% $CO_2$ atmosphere, the fluorescence emission was measured using SpectraMax® M5 (Molecular Devices, Sunnyvale, Calif.) (560EX nm/590 nm). The results are shown in in FIGS. 4 and 5.

Using the fluorescent emission, change in the viability of the cells may be calculated by comparing the ratio of the fluorescent emission of the treated cells to the untreated control cells. As shown by the results, cells treated with ECOBIDENS™ displayed a notably higher viability than non-pretreated control cells.

EXAMPLE 5

In this Example, a *Bidens* extract was analyzed for its ability to protect fibroblasts against UV- or $H_2O_2$-induced apoptosis.

Human dermal fibroblasts were grown to confluence in growth media (DMEM+10% FBS) and then treated for 12 hours with 3% v/v ECOBIDENS™ in growth media (DMEM (Life Technologies, Grand Island, N.Y.)+2% Fetal Bovine Serum (FBS) (Life Technologies)+1×antibiotic/antimycotic (AA)). Cells were washed with PBS and then samples of cells were further treated with either 200 μM $H_2O_2$ for 1 hour at 37° C. or irradiated with 100 mJ UV/cm². A sample of untreated cells was used as a control. Another sample of cells was not treated with ECOBIDENS™, but was treated with either $H_2O_2$ or UV (n=4). After further washing with PBS, cells were allowed to recover in media at 37° C. in 5% $CO_2$ atmosphere. After 12 hours, cells were stained with the apoptotic marker Annexin V Alexa Fluor 488 (Life Technologies, Grand Island, N.Y.) (fluorescent emission reported as Annexin). The results are shown in FIGS. 6A-6F. Results represent two independent experiments analyzing 10,000 cells/reading.

As shown in FIGS. 6A-6F, ECOBIDENS™ prevented the increase in early apoptotic markers caused by the UV and/or $H_2O_2$ insults. Also, FSC and HSC values (size and granularity) indicated a decrease in percentage of apoptotic cells in ECOBIDENS™-treated samples.

EXAMPLE 6

In this Example, a *Bidens* extract was analyzed for its ability to minimize the decrease in cellular glutathione (GSH) concentration due to UV irradiation or $H_2O_2$-induced stress.

Human dermal fibroblasts were grown to confluence in growth media (DMEM+10% FBS) and then treated for 24 hours with 3% v/v ECOBIDENS™ in growth media (DMEM (Life Technologies, Grand Island, N.Y.)+2% Fetal Bovine Serum (FBS) (Life Technologies)+1×antibiotic/antimycotic (AA)). Cells were washed with PBS and then samples of cells were further treated with either 200 μM $H_2O_2$ (n=4) for 1 hour at 37° C. or irradiated with 100 mJ UV/cm² (n=4). A sample of untreated cells (n=4) was used as a control. Another sample of cells was not treated with ECOBIDENS™, but was treated with either $H_2O_2$ or UV (n=4/treatment). After further washing the cells with PBS three times, cells were allowed to recover for approximately 20 hours in media (DMEM+10% FBS) at 37° C. in 5% $CO_2$ atmosphere.

Cells were harvested by trypsinization and centrifuged in 1.5 ml tubes at 1500 rpm for 5 minutes at 4° C. to pellet the cells. The supernatant was discarded and cells were resuspended in PBS. Cells were then snap frozen by immersion in liquid nitrogen and thawed quickly in a 37° C. water bath. Four cycles of freeze-thaw were undertaken. The tubes were centrifuged at 10,000×g at 4° C. for 15 minutes. The supernatant was transferred to new 1.5 ml tubes and stored at −80° C. for reduced glutathione (GSH) analysis using the SENSOLYTE® Glutathione Cellular Assay Kit (AnaSpec, Inc., Fremont, Calif.). The results of the GSH analysis are shown in FIG. 7.

Figure 7:
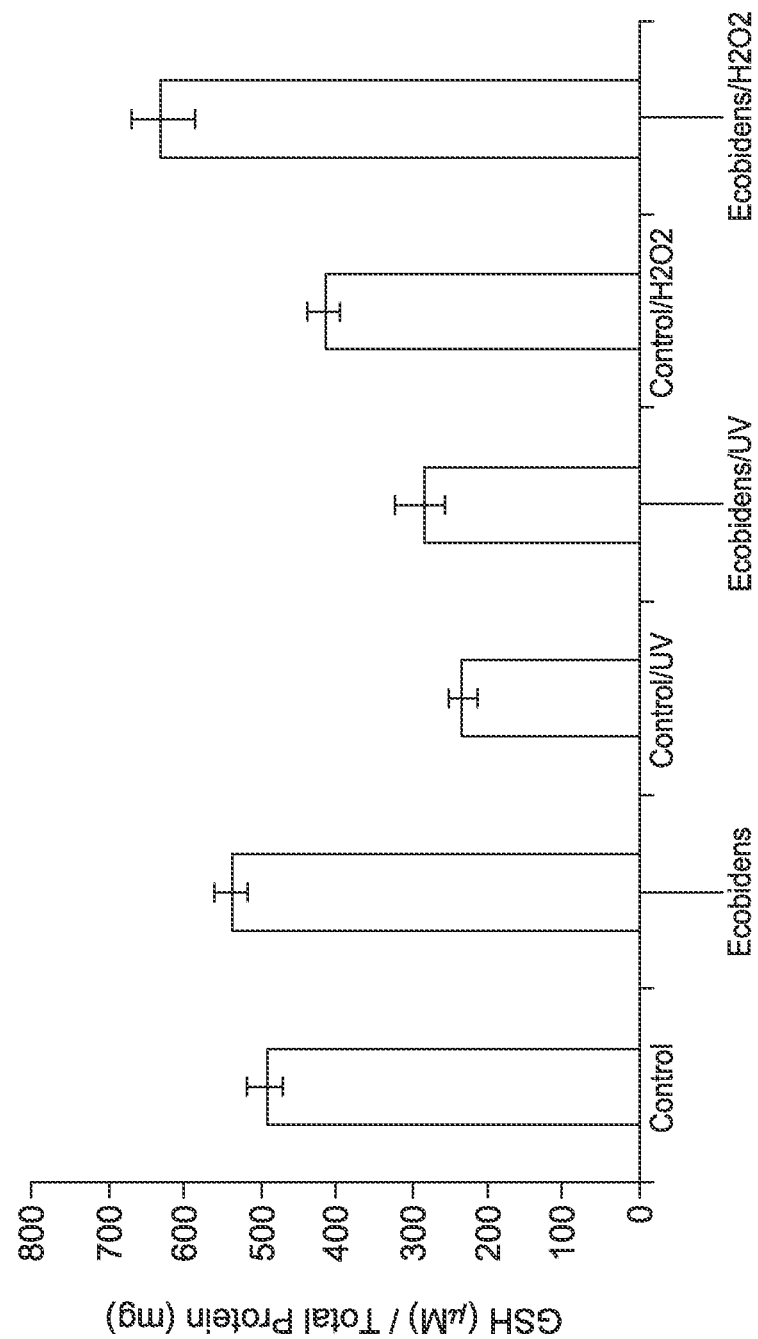
FIG. 7 is a graph depicting decreased cellular GSH concentration due to UV irradiation or $H_2O_2$-induced oxidative stress as analyzed in Example 6.

As shown in FIG. 7, both the UV and $H_2O_2$ insults caused a decrease in cellular GSH levels. The impact of $H_2O_2$ and UV insults on GSH levels, however, was minimized in the sample cells treated with ECOBIDENS™.

EXAMPLE 7

In this Example, the activity of a *Bidens* extract on $H_2O_2$ concentration was analyzed.

Primary human dermal fibroblasts were grown to confluence in growth media (DMEM+10% FBS) and then treated for 12 hours with 3% v/v ECOBIDENS™ in growth media (DMEM (Life Technologies, Grand Island, N.Y.)+2% Fetal Bovine Serum (FBS) (Life Technologies)+1×antibiotic/antimycotic (AA)). Three control samples were left untreated. N=4 for each treated and untreated sample. Cells of all samples were then washed twice with PBS. One control sample was treated at 37° C. with 200 μM $H_2O_2$; one control sample was treated at 37° C. with 200 μM $H_2O_2$ and catalase (available as Hydrogen Peroxide Cell-Based Assay Kit as used according to the manufacturer's instructions (Cayman Chemicals Company, Ann Arbo, Mich.)). An ECOBIDENS™-treated sample was also treated at 37° C. with 200 μM $H_2O_2$. After 1 hour of treatment with $H_2O_2$, $H_2O_2$ concentration in the sample was measured with a Hydrogen Peroxide Cell-Based Assay Kit (Cayman Chemicals Company, Ann Arbo, Mich.). More particularly, the kit measured fluorescence emission as being proportional to $H_2O_2$ concentration.

Figure 8:
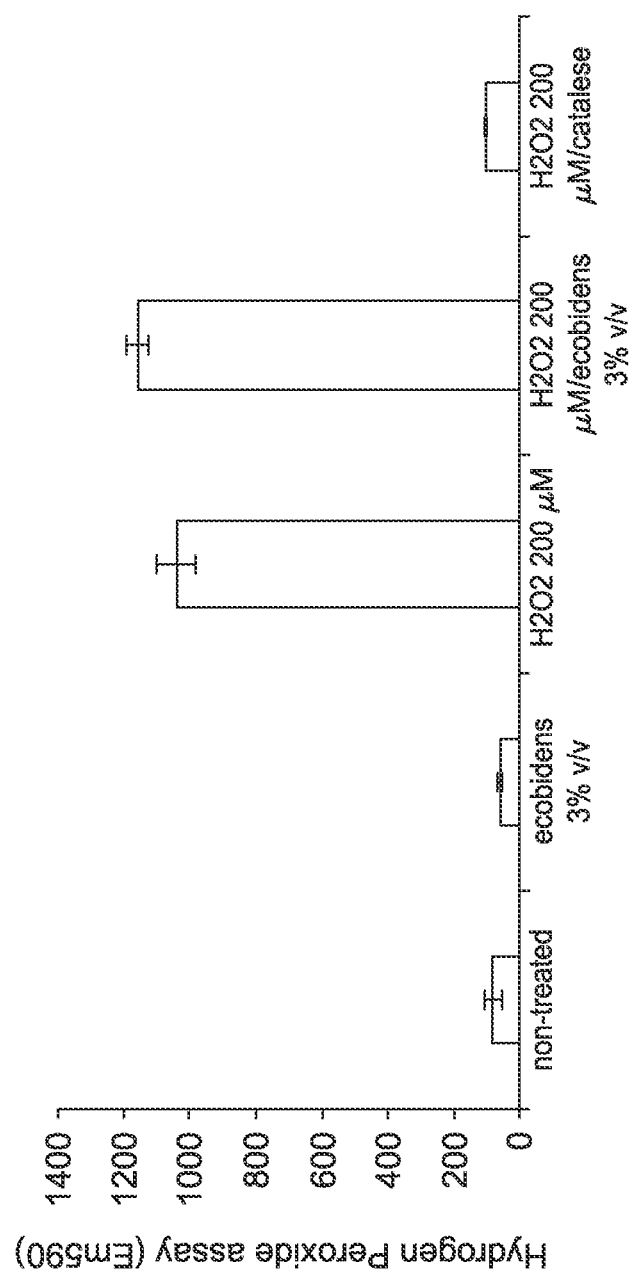
FIG. 8 is a graph depicting activity of ECOBIDENS™ on the concentration of $H_2O_2$ as analyzed in Example 7.

As shown in FIG. 8, pretreatment with a *Bidens* extract does not reduce the concentration of $H_2O_2$ in a sample. That is, as the *Bidens* extract is washed prior to treatment with $H_2O_2$, it has now been shown that residual amounts of the extract are not causing the reduction in $H_2O_2$. By contrast, it is believed that the extract enhances the cells own defense mechanisms to reduce the concentration of $H_2O_2$.

EXAMPLE 8

In this Example, extracts were analyzed for their ability to enhance cell resilience to UV irradiation and/or oxidative stress.

Primary human keratinocytes were grown to confluence in growth media (EpiLife® Medium, Life Technologies, Grand Island, N.Y., with 60 μM calcium (Gibco®, Life Technologies, Grand Island, N.Y.), supplemented with EpiLife® Defined Growth Supplement (EDGS) (Life Technologies, Grand Island, N.Y.) and 1×Antibiotics/antimycotics) and then treated for 12 hours with 3%, 6%, or 9% v/v of either UNDARINE™ or ECOBIDENS™. N=4 for each treated and untreated sample. One control sample was left untreated and another control sample was treated with 5 μM of rotenone. Cells were washed and then samples of cells were further treated with 200 μM $H_2O_2$ for 1 hour at 37° C. or irradiated with 100 mJ/cm² UV. Cells were allowed to recover in media (DMEM+10% FBS) at 37° C. in 5% $CO_2$ atmosphere. After 16 hours, cells were incubated in PBS+10% ALAMARBLUE® (Life Technologies, Grand Island, N.Y.) for 1 hour at 37° C. in 5% $CO_2$ and fluorescence emission was measured using SpectraMax® M5 (Molecular Devices, Sunnyvale, Calif.) (560EX nm/590 nm). The results are shown in FIGS. 9 and 10.

Figure 9:
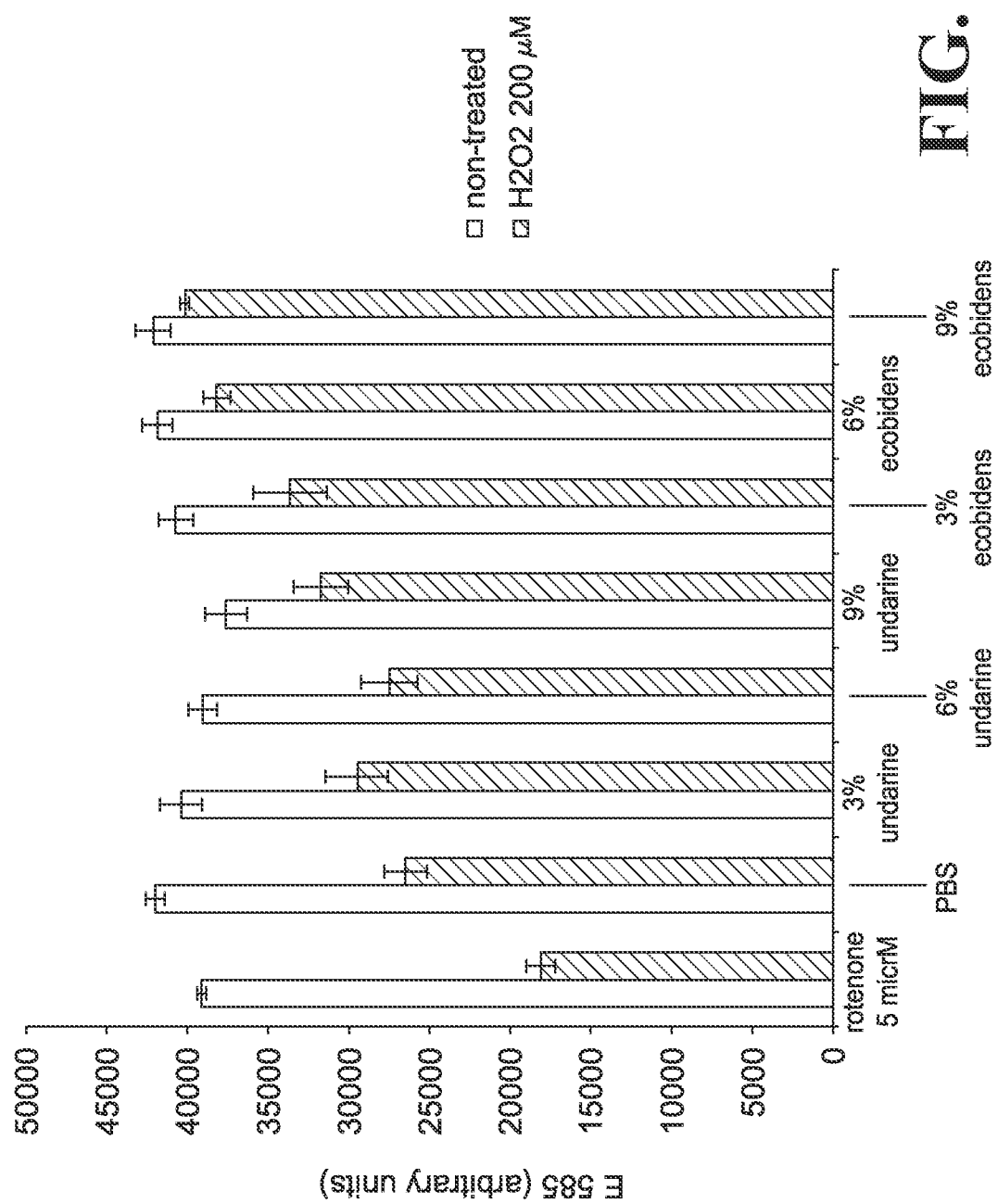
FIG. 9 is a graph depicting fluorescence emission as an indicator of $H_2O_2$-induced oxidative stress as analyzed in Example 8.
Figure 10:
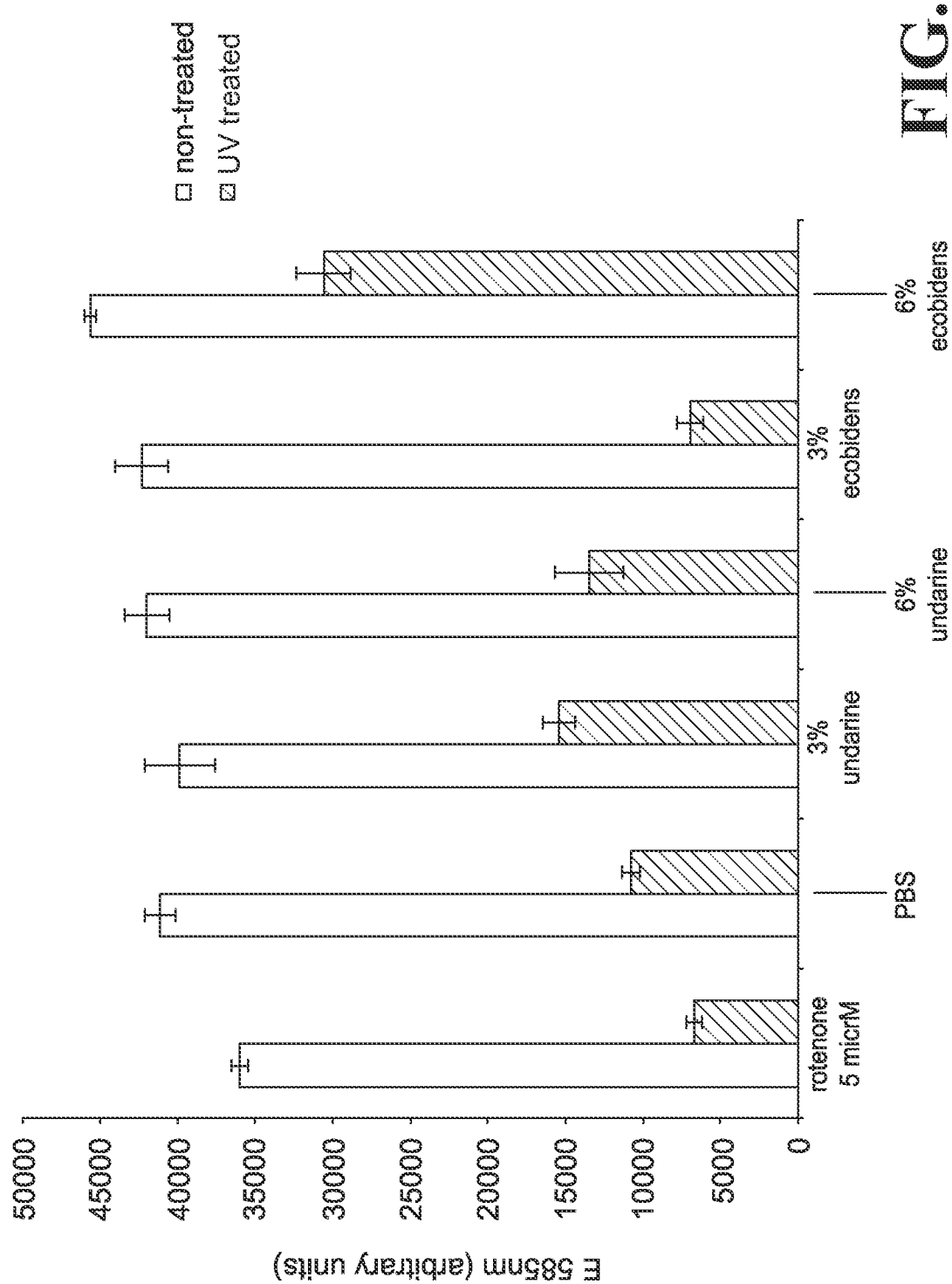
FIG. 10 is a graph depicting fluorescence emission as an indicator of UV exposure as analyzed in Example 8.

As shown in FIGS. 9 and 10, both UNDARINE™ and ECOBIDENS™ protected the cells from $H_2O_2$ and/or UV exposure. It is believed that both UNDARINE™ and ECOBIDENS™ enhanced keratinocyte resilience to oxidative stress caused by $H_2O_2$ treatment and/or UV irradiation by enhancing cellular mitochondrial activity and/or antioxidant cellular response.

The above Examples show that both *Undaria* and *Bidens* extracts are effective in protecting cells from photo-damage and oxidative stress. Accordingly, compositions including these extracts can be topically applied to protect cells from UV exposure and excessive production of ROS, thereby resulting in a more youthful appearance of aged skin of the face and body. It is believed that these protective effects are due to *Undaria* and *Bidens* being capable of enhancing cellular defense mechanisms, and in particular, cellular mitochondrial activity and antioxidant cellular response, thereby minimizing cell degeneration and death. These effects have proven to slow and/or reduce the process of skin aging and its the symptoms (e.g., skin thinning, sagging, wrinkling, fragility, and loss of skin resiliency).

What is claimed is:

1. A method for reducing oxidative stress of cells in an individual in need thereof, the method comprising: topically applying a composition that comprises from 0.1% (w/w) to 5% (w/w) of an *Undaria* extract, from 0.1% (w/w) to 5% (w/w) of a *Bidens* extract, and a hydrophilic carrier to a target skin region of the individual, wherein the cells are selected from the group consisting of dermal fibroblasts and epidermal keratinocytes;

and wherein the *Undaria* and *Bidens* extracts have not been further supplemented for fucoidan content.

2. The method of claim 1 wherein the target skin region is selected from the group consisting of facial skin, neck skin, breast skin, shoulder skin, chest skin, leg skin, hand skin, feet skin, and combinations thereof.

3. The method of claim 1 wherein the *Undaria* extract is selected from the group consisting of *Undaria crenata*, *Undaria peterseniana*, *Undaria pinnatifida*, *Undaria undarioides*, and combinations thereof.

4. The method of claim 1 wherein the *Bidens* extract is selected from the group consisting of *Bidens alba*, *Bidens amplectens*, *Bidens amplissima*, *Bidens aristosa*, *Bidens asymmetrica*, *Bidens aurea*, *Bidens beckii*, *Bidens bidentoides*, *Bidens bigelovii*, *Bidens bipinnata*, *Bidens biternata*, *Bidens campylotheca*, *Bidens cernua*, *Bidens cervicata*, *Bidens chippii*, *Bidens conjuncta*, *Bidens connata*, *Bidens coronata*, *Bidens cosmoides*, *Bidens cynapiifolia*, *Bidens discoidea*, *Bidens eatonii*, *Bidens ferulifolia*, *Bidens forbesii*, *Bidens frondosa*, *Bidens gardneri*, *Bidens hawaiensis*, *Bidens henryi*, *Bidens heterodoxa*, *Bidens heterosperma*, *Bidens hillebrandiana*, *Bidens hyperborean*, *Bidens laevis*, *Bidens lemmonii*, *Bidens leptocephala*, *Bidens leptophylla*, *Bidens macrocarpa*, *Bidens mannii*, *Bidens mauiensis*, *Bidens maximowicziana*, *Bidens menziesii*, *Bidens micrantha*, *Bidens mitis*, *Bidens molokaiensis*, *Bidens x multticeps*, *Bidens parviflora*, *Bidens pilosa*, *Bidens polylepis*, *Bidens*

*populifolia, Bidens radiate, Bidens reptans, Bidens sandvicensis, Bidens schimperi, Bidens simplicifolia, Bidens socorrensis, Bidens squarrosa, Bidens subalternans, Bidens tenuisecta, Bidens torta, Bidens trichosperma, Bidens tripartita, Bidens triplinervia, Bidens valida, Bidens vulgata, Bidens wiebkei*, and combinations thereof.

5. A method for reducing oxidative stress-induced apoptosis of cells in an individual in need thereof, the method comprising: topically applying a composition that comprises from 0.1% (w/w) to 5% (w/w) of an *Undaria* extract, from 0.1% (w/w) to 5% (w/w) of a *Bidens* extract, and a hydrophilic carrier to a target skin region of the individual, wherein the cells are selected from the group consisting of dermal fibroblasts and epidermal keratinocytes; and wherein the *Undaria* and *Bidens* extracts have not been further supplemented for fucoidan content.

6. The method of claim 5 wherein the target skin region is selected from the group consisting of facial skin, neck skin, breast skin, shoulder skin, chest skin, leg skin, hand skin, feet skin, and combinations thereof.

7. The method of claim 5 wherein the *Undaria* extract is selected from the group consisting of *Undaria crenata, Undaria perseniana, Undaria pinnatifida, Undaria undarioides*, and combinations thereof.

8. The method of claim 5 wherein the *Bidens* extract is selected from the group consisting of *Bidens alba, Bidens amplectens, Bidens amplissima, Bidens aristosa, Bidens asymmetrica, Bidens aurea, Bidens beckii, Bidens bidentoides, Bidens bigelovii, Bidens bipinnata, Bidens biternata, Bidens campylotheca, Bidens cernua, Bidens cervicata, Bidens chippii, Bidens conjuncta, Bidens connata, Bidens coronata, Bidens cosmoides, Bidens cynapiifolia, Bidens discoidea, Bidens eatonii, Bidens ferulifolia, Bidens forbesii, Bidens frondosa, Bidens gardneri, Bidens hawaiensis, Bidens henryi, Bidens heterodoxa, Bidens heterosperma, Bidens hillebrandiana, Bidens hyperborean, Bidens laevis, Bidens lemmonii, Bidens leptocephala, Bidens leptophylla, Bidens macrocarpa, Bidens mannii, Bidens mauiensis, Bidens maximowicziana, Bidens menziesii, Bidens micrantha, Bidens mitis, Bidens molokaiensis, Bidens x multticeps, Bidens parviflora, Bidens pilosa, Bidens polylepis, Bidens populifolia, Bidens radiate, Bidens reptans, Bidens sandvicensis, Bidens schimperi, Bidens simplicifolia, Bidens socorrensis, Bidens squarrosa, Bidens subalternans, Bidens tenuisecta, Bidens torta, Bidens trichosperma, Bidens tripartita, Bidens triplinervia, Bidens valida, Bidens vulgata, Bidens wiebkei*, and combinations thereof.

9. A method for reducing photodamage of cells in an individual in need thereof, the method comprising: topically applying a composition that comprises from 0.1% (w/w) to 5% (w/w) of an *Undaria* extract, from 0.1% (w/w) to 5% (w/w) of a *Bidens* extract, and a hydrophilic carrier to a target skin region of the individual, wherein the cells are selected from the group consisting of dermal fibroblasts and epidermal keratinocytes; and
wherein the *Undaria* and *Bidens* extracts have not been further supplemented for fucoidan content.

10. The method of claim 9 wherein the *Undaria* extract is selected from the group consisting of *Undaria crenata, Undaria perseniana, Undaria pinnatifida, Undaria undarioides*, and combinations thereof.

11. The method of claim 9 wherein the *Bidens* extract is selected from the group consisting of *Bidens alba, Bidens amplectens, Bidens amplissima, Bidens aristosa, Bidens asymmetrica, Bidens aurea, Bidens beckii, Bidens bidentoides, Bidens bigelovii, Bidens bipinnata, Bidens biternata, Bidens campylotheca, Bidens cernua, Bidens cervicata, Bidens chippii, Bidens conjuncta, Bidens connata, Bidens coronata, Bidens cosmoides, Bidens cynapiifolia, Bidens discoidea, Bidens eatonii, Bidens ferulifolia, Bidens forbesii, Bidens frondosa, Bidens gardneri, Bidens hawaiensis, Bidens henryi, Bidens heterodoxa, Bidens heterosperma, Bidens hillebrandiana, Bidens hyperborean, Bidens laevis, Bidens lemmonii, Bidens leptocephala, Bidens leptophylla, Bidens macrocarpa, Bidens mannii, Bidens mauiensis, Bidens maximowicziana, Bidens menziesii, Bidens micrantha, Bidens mitis, Bidens molokaiensis, Bidens x multticeps, Bidens parviflora, Bidens pilosa, Bidens polylepis, Bidens populifolia, Bidens radiate, Bidens reptans, Bidens sandvicensis, Bidens schimperi, Bidens simplicifolia, Bidens socorrensis, Bidens squarrosa, Bidens subalternans, Bidens tenuisecta, Bidens torta, Bidens trichosperma, Bidens tripartita, Bidens triplinervia, Bidens valida, Bidens vulgata, Bidens wiebkei*, and combinations thereof.

12. The method of claim 1 wherein the composition further includes beta-sitosterol.

13. The method of claim 12, wherein the beta-sitosterol is present in the composition in an amount of from about 0.001% by weight of the composition to about 10.0% by weight of the composition.

14. The method of claim 1, wherein the composition further includes a vasodilator.

15. The method of claim 14, wherein the vasodilator is selected from the group consisting of glyceryl trinitrate, resveratrol, caffeine, ginger extract, *ginseng* and combinations thereof.

16. The method of claim 5 wherein the composition further includes beta-sitosterol.

17. The method of claim 16, wherein the beta-sitosterol is present in the composition in an amount of from about 0.001% by weight of the composition to about 10.0% by weight of the composition.

18. The method of claim 5, wherein the composition further includes a vasodilator.

19. The method of claim 18, wherein the vasodilator is selected from the group consisting of glyceryl trinitrate, resveratrol, caffeine, ginger extract, *ginseng* and combinations thereof.

20. The method of claim 9 wherein the composition further includes beta-sitosterol.

21. The method of claim 20, wherein the beta-sitosterol is present in the composition in an amount of from about 0.001% by weight of the composition to about 10.0% by weight of the composition.

22. The method of claim 9, wherein the composition further includes a vasodilator.

23. The method of claim 22, wherein the-vasodilator is selected from the group consisting of glyceryl trinitrate, resveratrol, caffeine, ginger extract, *ginseng* and combinations thereof.

24. The method of claim 1, wherein the composition further comprises a polar co-solvent, and wherein the polar co-solvent is selected from the group consisting of glycerin, propanediol, ethanol, propylene glycol, butanol, isopropanol, propanol, dimethyl isosorbide, butylene glycol, polyethylene glycol, dipropylene glycol, ethoxydiglycol, pentylene glycol, and combinations thereof.

25. The method of claim 5, wherein the composition further comprises a polar co-solvent, and wherein the polar co-solvent is selected from the group consisting of glycerin, propanediol, ethanol, propylene glycol, butanol, isopropanol, propanol, dimethyl isosorbide, butylene glycol, polyethylene glycol, dipropylene glycol, ethoxydiglycol, pentylene glycol, and combinations thereof.

26. The method of claim 9, wherein the composition further comprises a polar co-solvent, and wherein the polar co-solvent is selected from the group consisting of glycerin, propanediol, ethanol, propylene glycol, butanol, isopropanol, propanol, dimethyl isosorbide, butylene glycol, polyethylene glycol, dipropylene glycol, ethoxydiglycol, pentylene glycol, and combinations thereof.

* * * * *